United States Patent
Zeetser et al.

(10) Patent No.: US 9,693,812 B2
(45) Date of Patent: *Jul. 4, 2017

(54) BONE PLATE FOR REDUCING ANGULAR BONE DEFORMITY AND METHOD OF USING

(71) Applicant: FastForward Surgical Inc., Henderson, NV (US)

(72) Inventors: Vladimir Zeetser, Tarzana, CA (US); Dawn Buratti, Malibu, CA (US)

(73) Assignee: FastForward Surgical Inc., Henderson, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/905,433

(22) PCT Filed: Jul. 16, 2014

(86) PCT No.: PCT/US2014/046824
§ 371 (c)(1),
(2) Date: Jan. 15, 2016

(87) PCT Pub. No.: WO2015/009808
PCT Pub. Date: Jan. 22, 2015

(65) Prior Publication Data
US 2016/0157904 A1    Jun. 9, 2016

Related U.S. Application Data

(60) Provisional application No. 61/846,760, filed on Jul. 16, 2013.

(51) Int. Cl.
*A61B 17/80* (2006.01)
*A61B 17/82* (2006.01)
(Continued)

(52) U.S. Cl.
CPC ...... *A61B 17/8061* (2013.01); *A61B 17/0469* (2013.01); *A61B 17/82* (2013.01); *A61B 17/842* (2013.01); *A61B 2017/565* (2013.01)

(58) Field of Classification Search
CPC . A61B 17/80; A61B 17/8033; A61B 17/8038; A61B 17/8042; A61B 17/8047;
(Continued)

(56) References Cited

U.S. PATENT DOCUMENTS

| 1,665,030 A | 4/1928 | Hartwig |
| 1,746,865 A | 2/1930 | Page |

(Continued)

FOREIGN PATENT DOCUMENTS

| WO | WO 2008/019511 A1 | 2/2008 |
| WO | WO 2009/086397 A2 | 7/2009 |

OTHER PUBLICATIONS

International Search Report and Written Opinion dated Nov. 24, 2014 for PCT/US2014/046824.

(Continued)

*Primary Examiner* — Si Ming Ku
(74) *Attorney, Agent, or Firm* — Knobbe, Martens, Olson & Bear LLP

(57) ABSTRACT

Described herein are methods and devices for the correction and reduction of bone deformities, such as metatarsus primus adductus, using a tethering technique which does not require drilling into the stable bone. In some embodiments, a bone plate has an elongate plate body and wings extending laterally from the plate body. The wings may be configured to generally follow the circumferential contours of the bone when placed on the bone in use. The bone plate can further include means for positioning cerclage material on the bone plate such that the cerclage material extends circumferentially over the wings rather than on the bone, thereby (Continued)

reducing the total contact area between the cerclage material and the bone.

25 Claims, 23 Drawing Sheets

(51) Int. Cl.
*A61B 17/84* (2006.01)
*A61B 17/04* (2006.01)
*A61B 17/56* (2006.01)

(58) Field of Classification Search
CPC .. A61B 17/8061; A61B 17/82; A61B 17/0469
See application file for complete search history.

(56) References Cited

U.S. PATENT DOCUMENTS

| | | | |
|---|---|---|---|
| 2,596,038 A | 5/1952 | Mayer | |
| 2,706,023 A | 4/1955 | Merritt | |
| 2,958,324 A | 11/1960 | Berkemann | |
| 4,583,303 A | 4/1986 | Laiacona et al. | |
| 4,644,940 A | 2/1987 | Nakamura | |
| 5,190,545 A | 3/1993 | Corsi et al. | |
| 5,222,977 A * | 6/1993 | Esser | A61B 17/0469 606/144 |
| 5,282,782 A | 2/1994 | Kasahara | |
| 5,529,075 A | 6/1996 | Clark | |
| 5,743,913 A | 4/1998 | Wellisz | |
| 5,843,085 A | 12/1998 | Graser | |
| 6,318,373 B1 | 11/2001 | Kasahara | |
| 6,391,031 B1 | 5/2002 | Toomey | |
| 6,520,965 B2 | 2/2003 | Chervitz et al. | |
| 6,629,943 B1 | 10/2003 | Schroder | |
| 6,746,450 B1 | 6/2004 | Wall et al. | |
| 6,964,645 B1 | 11/2005 | Smits | |
| 7,344,538 B2 | 3/2008 | Myerson et al. | |
| 7,582,088 B2 | 9/2009 | Marissen et al. | |
| 7,875,058 B2 | 1/2011 | Holmes | |
| 7,901,431 B2 | 3/2011 | Shumas | |
| 8,057,522 B2 * | 11/2011 | Rothman | A61B 17/8042 606/289 |
| 8,221,455 B2 | 7/2012 | Shumas | |
| 8,257,403 B2 | 9/2012 | Den Hartog et al. | |
| 8,257,406 B2 | 9/2012 | Kay et al. | |
| 8,398,678 B2 | 3/2013 | Baker et al. | |
| 8,821,551 B2 | 9/2014 | Zeetser et al. | |
| 8,998,904 B2 | 4/2015 | Zeetser et al. | |
| 2004/0127907 A1 | 7/2004 | Dakin et al. | |
| 2005/0021033 A1 | 1/2005 | Zeiler et al. | |
| 2005/0049593 A1 | 3/2005 | Duong et al. | |
| 2006/0241607 A1 | 10/2006 | Myerson et al. | |
| 2006/0241608 A1 | 10/2006 | Myerson et al. | |
| 2008/0008777 A1 | 1/2008 | Radovic | |
| 2008/0155731 A1 | 7/2008 | Kasahara | |
| 2008/0177302 A1 | 7/2008 | Shurnas | |
| 2008/0269806 A1 | 10/2008 | Zhang et al. | |
| 2009/0036893 A1 | 2/2009 | Kartalian et al. | |
| 2009/0076617 A1 | 3/2009 | Ralph et al. | |
| 2009/0210010 A1 | 8/2009 | Strnad et al. | |
| 2009/0222047 A1 | 9/2009 | Graham | |
| 2009/0254190 A1 | 10/2009 | Gannoe et al. | |
| 2010/0036430 A1 | 2/2010 | Hartdegen et al. | |
| 2010/0094294 A1 | 4/2010 | Gillard et al. | |
| 2010/0094428 A1* | 4/2010 | Ralph | A61B 17/688 623/17.19 |
| 2010/0106110 A1 | 4/2010 | De Luca | |
| 2010/0125297 A1 | 5/2010 | Guederian et al. | |
| 2010/0152752 A1 | 6/2010 | Denove et al. | |
| 2010/0211071 A1 | 8/2010 | Lettmann et al. | |
| 2010/0211075 A1 | 8/2010 | Stone | |
| 2010/0234896 A1 | 9/2010 | Lorenz et al. | |
| 2010/0249687 A1 | 9/2010 | Goswami et al. | |
| 2010/0262194 A1 | 10/2010 | Wagner et al. | |
| 2011/0061664 A1 | 3/2011 | Paris Mayans Carlos | |
| 2011/0077656 A1 | 3/2011 | Sand et al. | |
| 2011/0082405 A1 | 4/2011 | Domangue et al. | |
| 2011/0118780 A1 | 5/2011 | Holmes, Jr. | |
| 2011/0119807 A1 | 5/2011 | Dellacorte et al. | |
| 2011/0130789 A1 | 6/2011 | Shurnas et al. | |
| 2011/0178557 A1 | 7/2011 | Rush et al. | |
| 2011/0224729 A1 | 9/2011 | Baker | |
| 2011/0301648 A1 | 12/2011 | Lofthouse et al. | |
| 2012/0016426 A1 | 1/2012 | Robinson | |
| 2012/0071935 A1 | 3/2012 | Keith et al. | |
| 2012/0215147 A1 | 8/2012 | Lunnon | |
| 2012/0330322 A1 | 12/2012 | Sand et al. | |
| 2015/0282849 A1 | 10/2015 | Zeetser et al. | |

OTHER PUBLICATIONS

International Search Report and Written Opinion in Application No. PCT/US2013/050687, mailed Sep. 6, 2013, 15 pages.

* cited by examiner

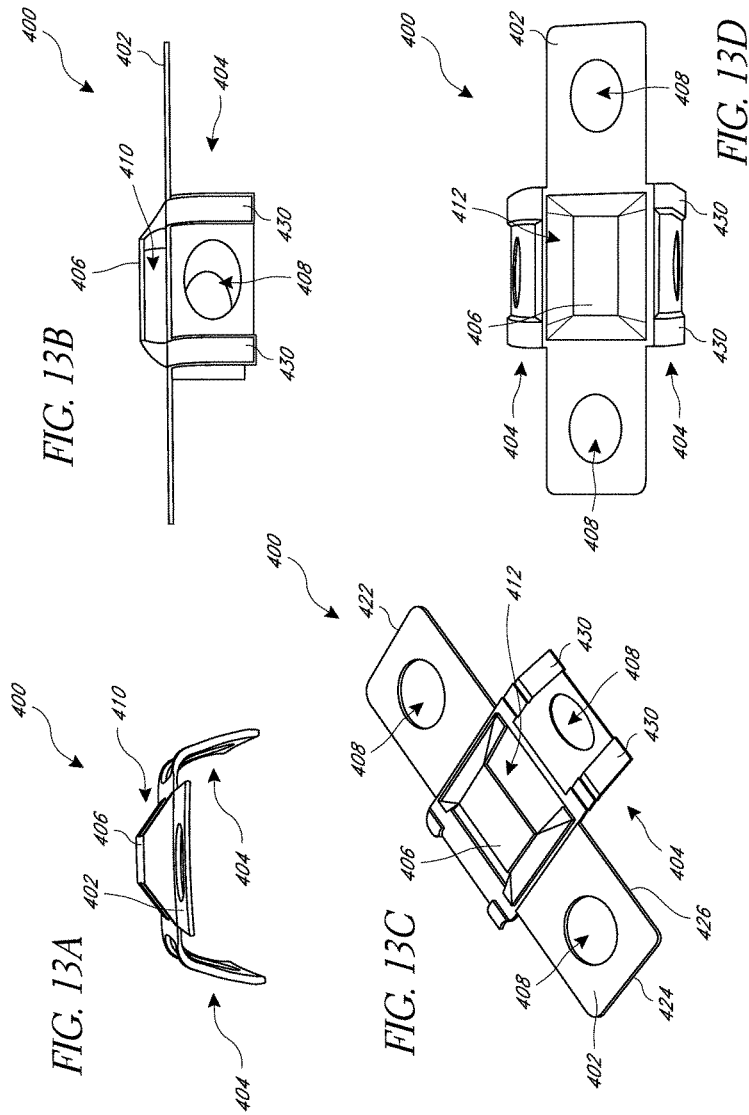

BONE PLATE FOR REDUCING ANGULAR BONE DEFORMITY AND METHOD OF USING

INCORPORATION BY REFERENCE TO ANY PRIORITY APPLICATIONS

This application is a National Phase Application of PCT International Application Number PCT/US2014/046824, filed Jul. 16, 2014, which claims the benefit of U.S. Provisional Application No. 61/846,760, filed Jul. 16, 2013, the entirety of which is hereby incorporated by reference. The disclosure of this application is also related to U.S. Provisional Application No. 61/672,297 filed on Jul. 17, 2012, U.S. Provisional Application No. 61/713,443 filed on Oct. 12, 2012, and to U.S. application Ser. No. 13/720,826, filed Dec. 19, 2012 and published as 2014/0025123 A1 on Jan. 23, 2014. Each of these applications is hereby incorporated by reference in its entirety.

BACKGROUND OF THE INVENTION

Field of the Invention

Embodiments of the invention relate to surgical implant devices for repairing or reducing angular bone deformities. In some embodiments, the devices can be used for reducing angular bone deformities such as metatarsus primus adductus. While certain embodiments of the invention were conceived for the purposes of correcting metatarsus primus adductus, it is conceivable that other embodiments can be adapted to correct other bone deformities as long as there is a stable bone somewhat adjacent to an unstable bone.

Description of the Related Art

Various angular bone deformities can affect human bones, including, for example, bones of the foot. For example, metatarsus primus adductus is a progressive angular deformity in the foot, between the first and second metatarsals, when the unstable or hypermobile first metatarsal deviates medially, increasing the intermetatarsal angle between the first and second metatarsals. Surgical procedures to correct this condition are chosen based on the severity of the angular deformity. Traditionally, surgical correction of moderate to severe angular deformities between the first and second metatarsals involves bone remodeling, osteotomies, wedge resection of bone or joint fusions, which cause irreversible alterations to bone and joint structures. A more desirable technique is to anatomically correct the deformity by reducing the abnormally wide angle between the two metatarsals by tethering them closer together using suture like material. Known are U.S. Pat. Nos. 8,221,455, 7,901,431, 7,875,058, 5,529,075, and U.S. Patent Publication No. 2011/0224729.

U.S. Pat. Nos. 8,221,455, 7,901,431, 7,875,058 and U.S. Patent Publication No. 2011/0224729 are tethering techniques whereby fiberwire, a suture-like material, along with buttress plates and/or buttons are used to tether the first and second metatarsals closer together like a tightrope. These techniques require holes to be drilled through both the first and second metatarsals. The Mini Tightrope system by Arthrex is an example of the tethering technique. First, a hole is drilled through the first and second metatarsals. Next, a buttress plate is secured to the second metatarsal bone by passing the suture through holes in the plate and through holes in both bones, then reducing the angular deformity by tightening the suture using a button and suture knot located on the medial side of the first metatarsal. The Mini Tightrope FT system by Arthrex is another example of tethering technique which uses an anchor-suture-button complex, where a threaded anchor is drilled into the second metatarsal base and the suture thread is then passed through a hole in the first metatarsal and the angular deformity is reduced as the suture thread is tightened and secured with a suture knot and button located along the medial aspect of the first metatarsal. Both of these tethering techniques require drilling into both the second and first metatarsals. U.S. Pat. No. 5,529,075 is similar in that it too requires drilling through the first and second metatarsals. Instead of a flexible suture-anchor technique, this reference requires the installation of a rigid stabilizing member between the first and second metatarsal. However, each of these references suffers from one or more of the following disadvantages: a hole must be drilled into or through the second metatarsal, to secure one end of the tethering device while the other (medial) end of the tethering device is secured with a button.

Drilling a hole through the second metatarsal, which is significantly smaller in diameter by comparison to the first metatarsal, severely weakens the bone. To minimize weakening of the second metatarsal, the hole must be drilled through the centerline of the bone so that a maximum amount of bone remains above and below the hole. Nevertheless, drilling a hole through the centerline of the second metatarsal is especially difficult because it is done at an angle through a hole in the first metatarsal. Making the procedure more difficult, the drilling must be done with little or no visibility. A second metatarsal bone which has been drilled through is more vulnerable to stress and/or fracture from tension caused by the tethering techniques. Fracture of the second metatarsal is a common and potentially devastating complication of these tethering techniques. Additionally, the use of buttons and suture knots located along the medial aspect of the first metatarsal can cause irritation of tissue, knot loosening and skin irritation/breakdown from prominent components.

Some surgeons have attempted to avoid drilling into the second metatarsal via a modification of the tethering technique, known as lasso technique. With the lasso technique, no holes are drilled through the second metatarsal, and no buttress plate or button is used. Instead, suture tape (i.e. Fibertape) is tied around the second metatarsal in the form of a cow-hitch knot and then secured to the first metatarsal. While the lasso technique avoids drilling through the second metatarsal by instead looping suture tape around the metatarsal, the suture tie itself can cause periosteal reaction and bone callus formation in some patients due to friction between the suture tape and the bone. To avoid periosteal reaction, few surgeons use absorbable suture to tether the first and second metatarsals together, but once the suture finally absorbs there is likely some loss of correction and possible recurrence of angular deformity.

In various other situations, a surgeon might need or want to wrap or tie suture or cerclage material around a bone to reduce an angular bone deformity. In any such case, when tension is applied to the suture material and the suture material is anchored to the bone, contact between the suture material and the bone can have adverse effects on the bone, for example, periosteal reaction, bone callus formation, rope burn, and/or even fracture. Because of the aforementioned problems, there is a need for method and device for reducing angular bone deformities between two bones, using a tethering technique with a suture material which not only avoids the complications associated with drilling into the second metatarsal, but also avoids the friction and tension forces (i.e. rope-burn) associated with lasso-type techniques and which also avoids the complications associated with the prominent medial button and suture knot.

SUMMARY OF THE INVENTION

Embodiments of the present invention satisfy this need in the form of a method and device that allows for the correction and reduction of angular bone deformities using a tethering technique which does not require drilling into the stable bone. The devices and methods described herein can also allow for the reduction of angular bone deformities without requiring the placement of a prominent suture knot/button device medially along the unstable bone. For example, in some embodiments, the devices and methods described herein can be used to reduce angular bone deformities such as metatarsus primus adductus, hallux valgus, Tailor's bunion, and/or other angular bone deformities. In some embodiments, a bone plate has an elongate plate body and wings extending laterally from the plate body. In some embodiments, the wings are configured to generally follow the circumferential contours of the bone when placed on the bone in use. The bone plate can further include means for positioning cerclage material on the bone plate such that the cerclage material extends circumferentially over the wings rather than on the bone, thereby reducing the total contact area between the cerclage material and the bone. The wings therefore create a buttress effect between the cerclage material and bone.

One embodiment is a winged looped plate comprising a plate body with buttress wings and dorsal loop. The winged looped plate with incorporated dorsal loop can be affixed to a bone using the tension applied to cerclage material, without any drilling of holes for passing tethering material through the bone, which violates the strength of the bone. With the plate against the bone cortex, a cerclage technique can be used to tie or loop cerclage material, such as suture tape, fibertape, or wire, around the plate and bone. The cerclage material is passed through the dorsal loop on the outer surface of the plate, which keeps the cerclage material centered on the plate. The cerclage material is tied around the stable bone, such as the second metatarsal, using a lasso-type or cowhitch-type tie. Then, upon tightening the cerclage material, the plate would be firmly affixed to the bone under tension, thereby dispensing with the need to affix the plate to the bone with screws. Once the cerclage material is tied around the plate and stable bone, the free ends of the cerclage material are then fixated to the unstable bone, such as the first metatarsal in a tethering mechanism (with the angular deformity anatomically reduced), using knotless anchors (interference screws) thus avoiding the use of prominent buttons and suture knots that are components of all other comparative tethering methods. By using a cerclage technique to affix the winged looped plate to bone under tension, the stable bone, such as the second metatarsal, is protected not only from drill hole related stress fractures, but also from friction/shear forces (cortical reaction) associated with tying suture around bone with the suture material directly against the bone cortex without any shielding.

This method and device address the aforementioned existing problem of angular bone deformities, in particular metatarsus primus adductus, the underlying cause of hallux valgus/bunion deformities, by utilizing the winged looped plate of embodiments described herein, placed directly against the stable bone, for example the second metatarsal bone.

The winged looped plate allows the surgeon to tie cerclage material around the plate protecting the underlying bone from both friction and tension forces from the cerclage material, and eliminating the need for drilling through the stable bone such as the second metatarsal. The method in one embodiment uses the winged looped plate, cerclage material, a suture passing instrument and two tenodesis (interference) screws to achieve a true reduction of the angular deformity. The two bones are tethered together using a cerclage technique around the second metatarsal, with the winged looped plate protecting the second metatarsal, and knotless anchors, such as interference screws or tenodesis anchors, are used to fixate the free ends of the suture material into the first metatarsal. This method creates a button-less, knotless, fully adjustable and reversible angular deformity correction, while the plate protects the second metatarsal bone from the harmful effects of both tension and friction between the cerclage material and bone.

In some embodiments, a device for treating an angular bone deformity includes an elongate plate body, two buttress wings extending from opposite sides of the plate body, and a transverse opening located between the first and second ends of the plate body. The elongate plate body includes an inner surface configured to engage a patient's stable metatarsal, an outer surface, a first end, a second end, and a longitudinal axis extending between the first end and the second end. The longitudinal axis is configured to be parallel or substantially parallel with a length or the longitudinal axis of the stable metatarsal. Each of the buttress wings includes an inner surface configured to engage the stable metatarsal. The inner surfaces of the buttress wings at least partially face each other so that when the plate body and the buttress wings are placed against the stable metatarsal, the stable metatarsal is at least partially surrounded by the elongate plate body and the two buttress wings. The transverse opening extends perpendicular to the longitudinal axis of the plate body and the stable metatarsal, and is directly aligned with the two buttress wings such that when the plate body and the two buttress wings are placed against the stable metatarsal and cerclage material passes through the transverse opening and is tied around the stable metatarsal, and is then secured to the patient's unstable metatarsal, the cerclage material also extends over the two buttress wings. The device further includes raised ridges or flanges disposed along the buttress wings (for example along edges of the buttress wings) or a groove disposed within the center of the wings. The raised ridges or flanges or groove are configured to maintain the position of the cerclage material centered over the wings after the cerclage material passes through the transverse opening.

In some embodiments, the buttress wings are configured to prevent cerclage material from directly contacting the stable metatarsal, for example the cortical surfaces on the tension side of the second metatarsal, when cerclage material extends through the transverse opening and passes over the buttress wings to fixate the cerclage material to the patient's unstable metatarsal under tension. The buttress wings can extend outwardly away from the longitudinal axis of the plate body. In some embodiments, the buttress wings extend in a direction perpendicular or generally perpendicular to the longitudinal axis of the plate body. The plate body can further include first and second lateral sides extending parallel or substantially parallel with the longitudinal axis of the plate body. A first of the two buttress wings extends away from the first lateral side, and a second of the two buttress wings extends away from the second lateral side. In some embodiments, the buttress wings are configured to engage opposite cortices of the stable metatarsal, such as the second metatarsal. The plate body can be configured to engage a lateral side of the second metatarsal. The device can be secured to the stable (such as second) metatarsal using cerclage tensioning and therefore without drilling a hole in the stable metatarsal. In some embodiments the plate body and the two buttress wings have flat or substantially flat inner surfaces. Alternatively, the plate body and two buttress wings can have concave inner surfaces and convex outer surfaces.

The plate body and/or buttress wings can include one or more holes. In some embodiments, the transverse opening is centrally located between the first and second ends of the plate body. The transverse opening can be raised relative to the outer surface of the plate body, defined at least in part by a dorsal loop provided on or above the outer surface of the plate body. In embodiments including a dorsal loop, the dorsal loop can include a curved wall extending above the outer surface of the plate body or a flat wall extending above the outer surface of the plate body to create an arched or flat opening respectively. In some embodiments, the dorsal loop is fixed and immobile relative to the plate body. The plate body can also include a hole, beneath the dorsal loop, centrally positioned between the first and second ends of the plate body, and between the two buttress wings. In some embodiments, the plate body, two buttress wings, and dorsal loop are integrally formed from a single piece of material. In some embodiments, the plate body and two buttress wings are formed from a single piece of material, while the dorsal loop is added to the outer surface of the plate body.

In some embodiments, the two buttress wings are symmetrically positioned about the longitudinal axis. The two buttress wings can also be centrally located between the first and second ends of the plate body. In some embodiments, a longitudinal length of each of the buttress wings is shorter than a longitudinal length of the plate body between the first and second ends. In some embodiments, the device includes multiple pairs of buttress wings longitudinally spaced along the length of the plate body.

In some embodiments, a device for correction and reduction of angular deformities such as metatarsus primus adductus includes a winged loop plate. The winged looped plate includes a plate body with two wings extending out in opposite directions from a center portion of the plate body, a fixed loop centered along an outer surface of the plate body and equally between the two wings, and raised ridges or flanges disposed along the wings, for example, along the edges of the wings, or a groove disposed within the center of the wings. The plate is configured such that when the plate is placed against a bone, a cerclage technique can be used to loop cerclage material around the plate and bone by passing the cerclage material through the loop of the plate to keep the cerclage material centered on the plate, and the ridges, flanges, or groove keeps the cerclage material centered on the wings.

In some embodiments, a system for treating an angular bone deformity such metatarsus primus adductus includes a device as described herein along with cerclage material configured to extend through the transverse opening and configured to fix the unstable metatarsal relative to the stable metatarsal. The system can also include one or more screws configured to fix the cerclage material into the first metatarsal and/or a suture passing instrument.

While certain embodiments of the invention were conceived for the purposes of correcting metatarsus primus adductus, it is conceivable that other embodiments can be adapted to correct other deviation bone deformities as long as there is a stable bone somewhat adjacent to an unstable bone.

BRIEF DESCRIPTION OF THE DRAWINGS

FIGS. 13A-13D shows another embodiment of a device for correcting bone deformities such as metatarsus primus adductus.

DETAILED DESCRIPTION OF THE PREFERRED EMBODIMENTS

In various situations, a surgeon may need or wish to tie (or lasso) cerclage material around one bone then secure the other end of the cerclage material (under tension) to an adjacent bone for stabilization or to reduce an angular deformity between the two bones. However, if the cerclage material is tied around a bone and is in direct contact with that bone, then there is risk of fracturing that bone once tension is placed on the cerclage material. Furthermore, when some cerclage material, such as suture tape, is tied around unprotected bone and then anchored to another bone using a tethering technique, any motion between the two bones can cause friction between the cerclage material and the unprotected bone. This friction can cause adverse effects such as periosteal reaction (rope burn) and possible stress fracture. The winged bone plates described herein advantageously protect the bone from two harmful forces: tension and friction. The elongate plate body distributes tension forces along a longitudinal footprint of the plate body against the bone, increasing the surface area of applied tension thereby reducing the force upon the bone. The buttress wings shield the bone from friction and rope burn which the cerclage material may cause. In some embodiments, a bone plate includes an elongate plate body and buttress wings extending laterally from the plate body. The bone plate can further include features such as transverse grooves or ridges which run perpendicular to the long axis of the plate and parallel to the buttress wings, for positioning (for example, in some embodiments, centering) the cerclage material over the wings as the cerclage material courses circumferentially around the plate and underlying bone and the combined effect of the plate and wings partially shield the bone from the cerclage material.

Figure 1:
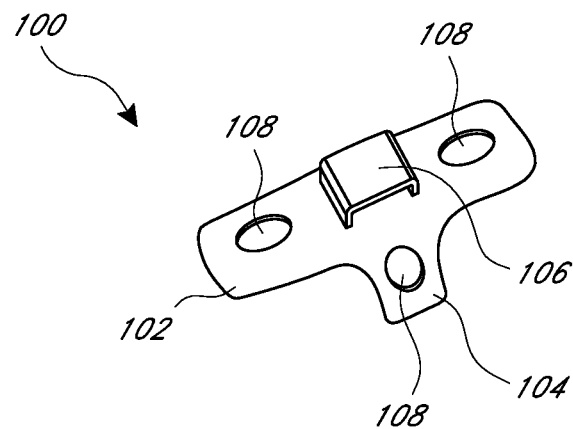
FIG. 1 is a perspective view of a device embodying features of a method and device for correcting bone deformities such as metatarsus primus adductus.
Figure 2:
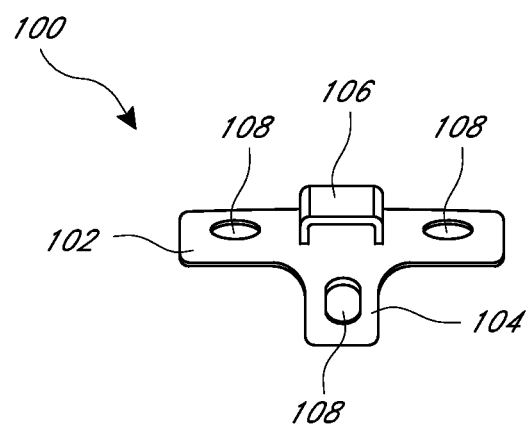
FIG. 2 is a side profile view of a device embodying features of a method and device for correcting bone deformities such as metatarsus primus adductus.
Figure 3:
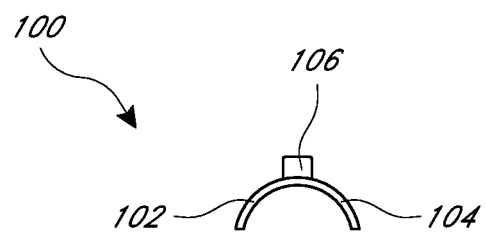
FIG. 3 is a front profile view of a device embodying features of a method and device for correcting bone deformities such as metatarsus primus adductus.
Figure 10:
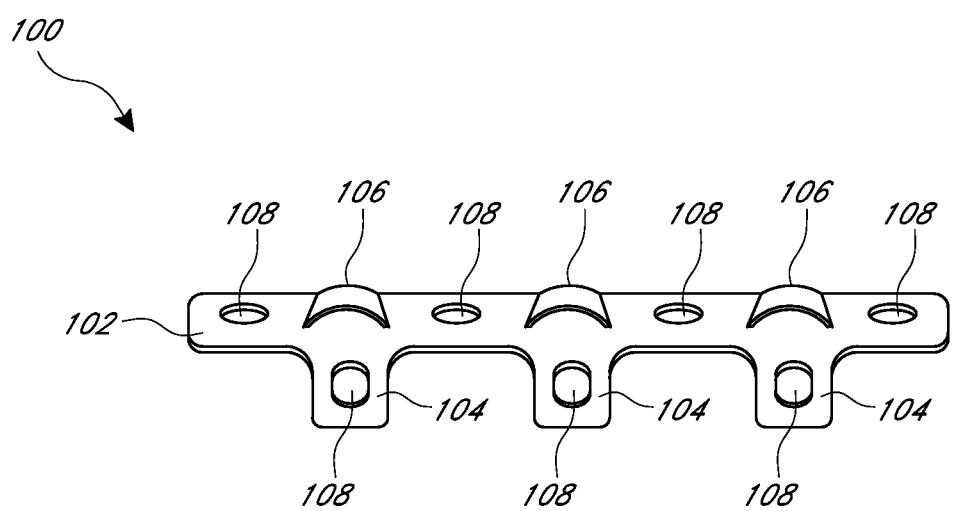
FIG. 10 is an alternate embodiment of the winged looped plate device embodying features for protection of a long bone when using any cerclage technique in a series as may be necessary for longer bones. An elongated version of the winged looped plate allows for multiple wings and multiple loops for applying a series of cerclage ties over a longer bone. This figure also shows a possible low-profile, arched variation of the dorsal loops if the cerclage material is thinner (i.e. monofilament wire).

FIGS. 1-3 illustrate one embodiment of the winged looped plate 100 device to correct bone deformities, in particular metatarsus primus adductus, the underlying cause of hallux valgus/bunion deformities. The winged looped plate 100 comprises a plate body 102 which is semi-tubular but can also be tubular, with buttress wings 104, a dorsal loop 106, and ingrowth holes 108. Depending on where the plate is to be used, the number of buttress wings 104, the number and shape of the dorsal loops 106, and size and number of holes 108 on the plate body can be customized. For example, several sets of buttress wings 104, dorsal loops 106, and ingrowth holes 108 can be arranged in series along a plate body for use in longer bones when a series of cerclage ties are needed. (FIG. 10). The plate body 102 is semi-tubular in shape with a convex outer surface and concave inner surface to conform to the contour of a long bone such as a metatarsal bone. The length of the plate body evenly distributes tension forces of the suture tape over a wider surface area (footprint) reducing stress on the bone. The plate body 102 comprises extension buttress wings 104 which project away and perpendicular to the long axis of the plate body, and each wing follows the circumferential contour of the long bone, further protecting the bone cortices where suture tape is tied circumferentially around the device and bone. The buttress wings are configured to be positioned under the cerclage material and to follow a portion of the circumferential path of the cerclage material, thereby creating a buttress effect to protect and shield the bone from harmful tension and friction. The plate body 102 and buttress wings 104 may have ingrowth holes 108 to allow scar tissue ingrowth for long-term stability of the plate position on the bone. The dorsal loop 106 extends from the outer convex surface of the plate body 102 to facilitate the threading of cerclage material, such as suture tape, fibertape, or wire, around the device. The dorsal loop 106 retains the cerclage material centered on the plate upon tightening to evenly secure the plate firmly against the bone under tension.

One embodiment can be fabricated to comprise the plate body 102, buttress wings 104, dorsal loop 106, and holes 108 using conventional manufacturing methods such as welding, pressing, casting, machining and/or forging. A variety of materials may be used including, metallics (i.e. titanium, stainless steel), bio absorbables (i.e. Poly-L-Lactide PLLA) or non-absorbables (i.e. PEEK polymer). Additionally, the inner surface of the winged looped plate 100 could be plasma coated or otherwise roughened for enhanced grip to bone.

Figure 4:
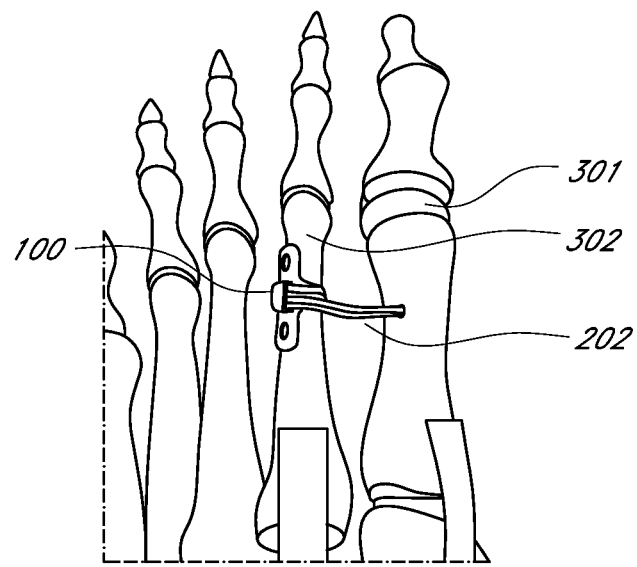
FIG. 4 is a top view of a skeleton embodying features of a method and device for correcting bone deformities such as metatarsus primus adductus.
Figure 5:
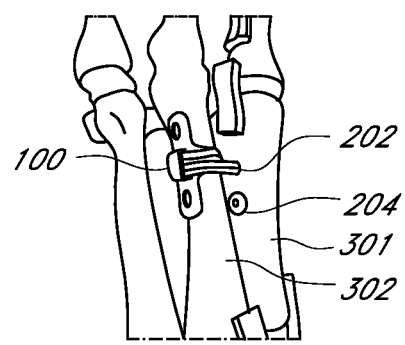
FIG. 5 is a profile view from the second metatarsal of a skeleton embodying features of a method and device for correcting bone deformities such as metatarsus primus adductus.
Figure 6:
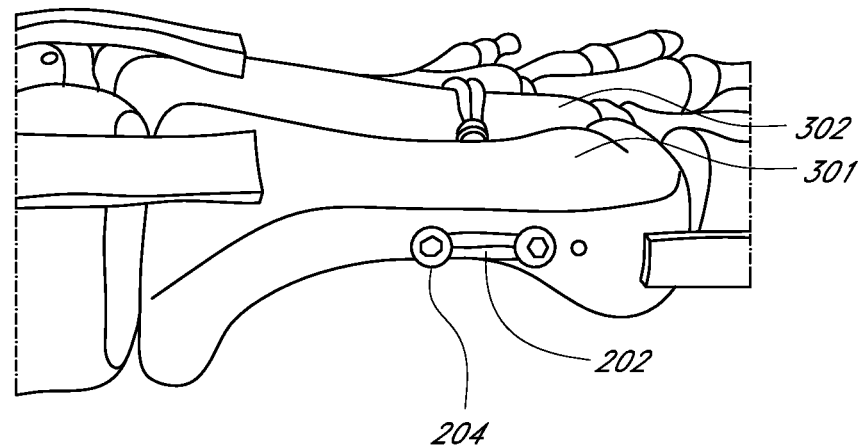
FIG. 6 is a profile view from the first metatarsal of a skeleton embodying features of a method and device for correcting bone deformities such as metatarsus primus adductus.
Figure 9:
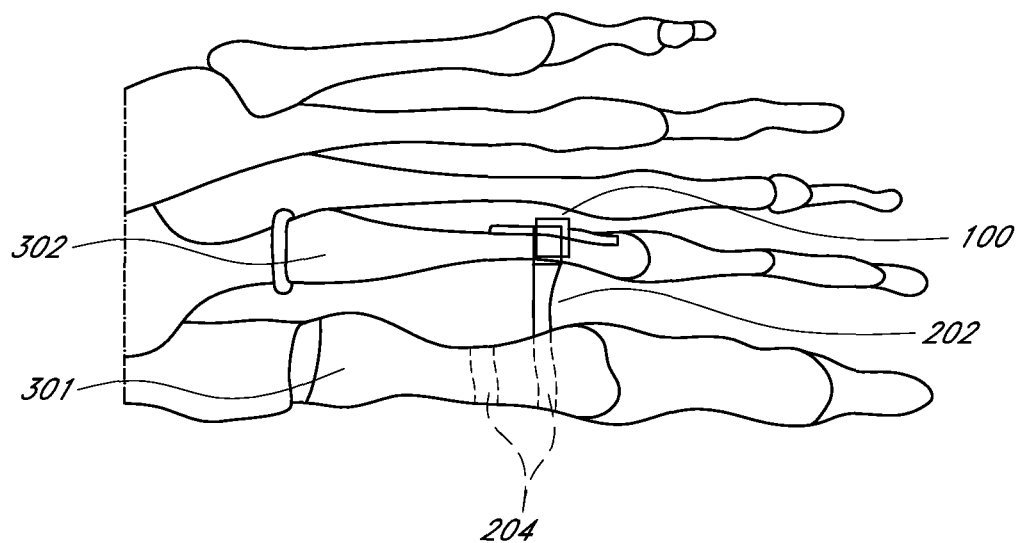
FIG. 9 is an illustration of the angular bone deformity, metatarsus primus adductus, anatomically reduced after the device and method is applied.
Figure 11:
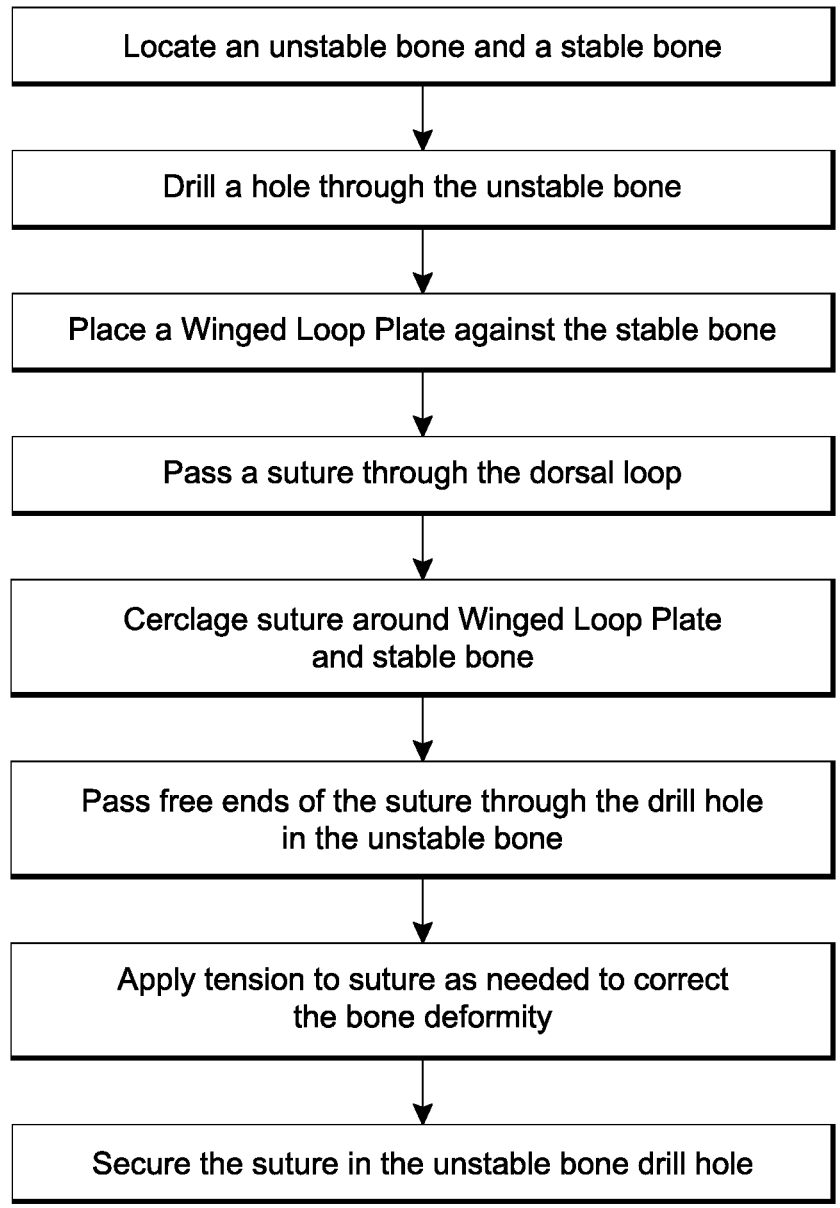
FIG. 11 is a flowchart illustrating a method for the correction of a bone deformity.

FIG. 11 is a flowchart illustrating the correction of a bone deformity using the method and device of the one embodiment. First, an unstable bone 301 and a stable bone 302 near the unstable bone 301 is located (FIG. 4). Second, a hole to accommodate a tenodesis (interference type) screw 204 is drilled through the unstable bone 301 (FIG. 5) so that an opening is formed on the side of the unstable bone that is furthest away from the stable bone (FIG. 9). Third, a winged looped plate 100 is placed with the inner surface against the stable bone 302 and with the dorsal loop 106 furthest away from the unstable bone 301 (FIG. 5). Fourth, a cerclage material 202 is passed through the dorsal loop 106 of the winged looped plate 100 on the stable bone 302 and tied around the stable bone 302 and winged looped plate 100 using a cerclage technique (FIG. 5). Fifth, the free ends of the cerclage material 202 are passed through the hole in the unstable bone 301 and tension is applied to the suture 202 to reduce the angular bone deformity (FIG. 6). Sixth, the cerclage material 202 is secured to the unstable bone 301 using a tenodesis (interference-type) screw 204 in the drill hole (FIG. 6).

Figure 7:
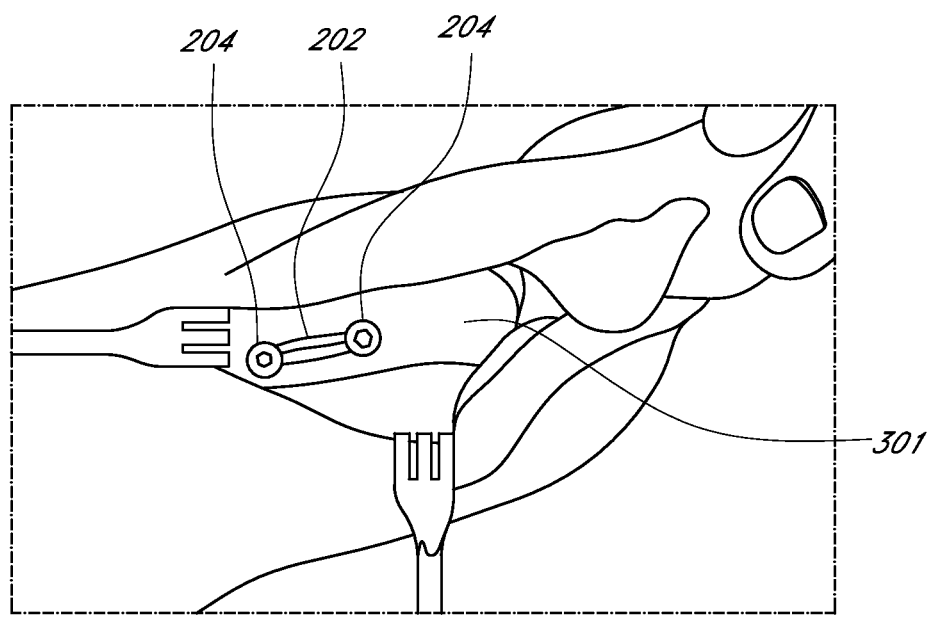
FIG. 7 is a profile view of a medial incision made along the first metatarsal with tenodesis (interference) screws anchoring the suture tape to the first metatarsal.

FIGS. 4-9 illustrate a method of using a winged looped plate 100 to correct the angular bone deformity, metatarsus primus adductus. First, an incision is made along the first metatarsal. 301 (the unstable bone) as best illustrated in FIG. 7. Second, a small incision is made dorsally adjacent to the second metatarsal 302 (the stable bone). Third, blunt dissection is used to create a tunnel through the soft tissue between the first metatarsal 301 and second metatarsal 302, connecting the two incisions. Third, cerclage material 202 is passed through the tunnel from medial to lateral, and located through the dorsal incision where it is then threaded through the dorsal loop 106 of the winged looped plate 100, which is then placed against the lateral cortex of the second metatarsal before the cerclage material 202 is tied once around the second metatarsal 302 using a cerclage technique, as best illustrated in FIGS. 4-5.

Figure 8:
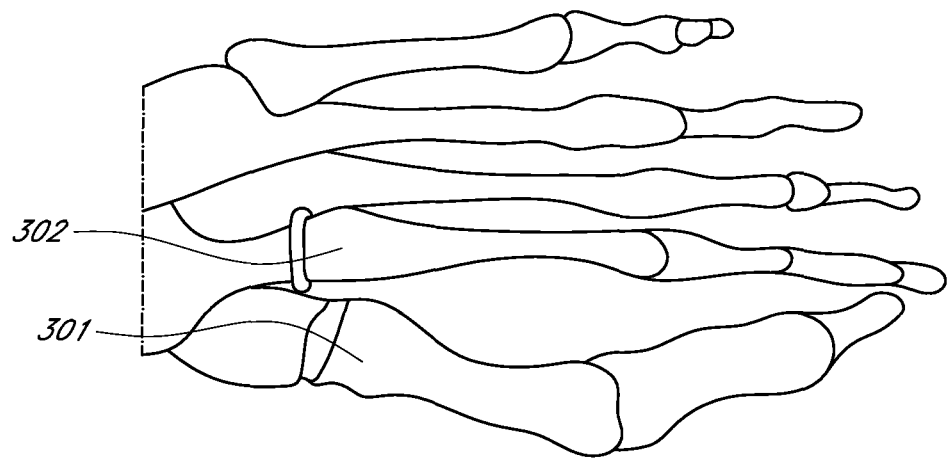
FIG. 8 is an illustration of the bone deformity, metatarsus primus adductus, before the device and method is applied.

Fourth, the cerclage material 202 is tightened so that the winged looped plate 100 is pressed firmly against the lateral aspect of the second metatarsal 302 and that buttress wings 104 of the plate cover and protect the dorsal and plantar cortices of the second metatarsal 302. The plate would be adhered to the bone primarily via tension from tightening the suture tape cerclage however, additional forms of optional fixation may include a single setscrew through a hole 108 in the dorsal wing 104, bone glue/paste/putty or other fixatives. Fifth, the free ends of the cerclage material 202 are then passed back through the soft tissue tunnel medially, then through a drill hole in the first metatarsal 301, from lateral to medial as illustrated in FIGS. 6-7. Sixth, the cerclage material 202 is pulled tightly through the drill hole, while reducing the intermetatarsal angular deformity to a more anatomic position, as illustrated in FIGS. 8-9. Seventh, a tenodesis anchor screw 204, shown in FIGS. 6-7, is inserted into the drill hole as an interference screw to secure the suture tape/cerclage material into the first metatarsal, maintaining tension across the tethering mechanism between the first and second metatarsals. Finally, a second point of fixation can be achieved by passing the remaining cerclage material 202 ends through a second drill hole in the first metatarsal and securing it into the bone by inserting a second interference screw 204.

Figure 12A:
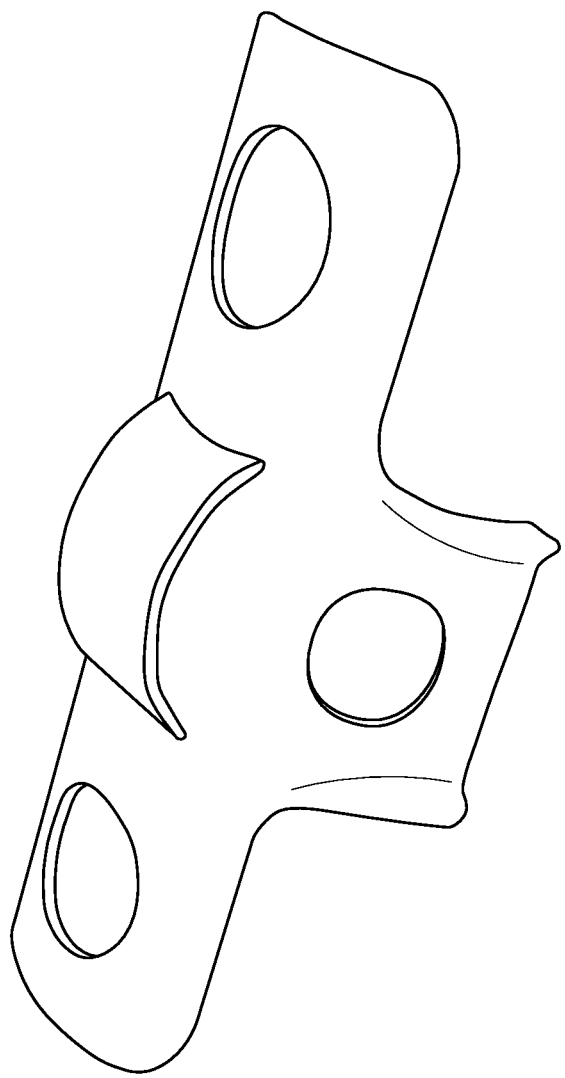
FIGS. 12A-12E shows another embodiment of a device for correcting bone deformities such as metatarsus primus adductus.
Figure 12B:
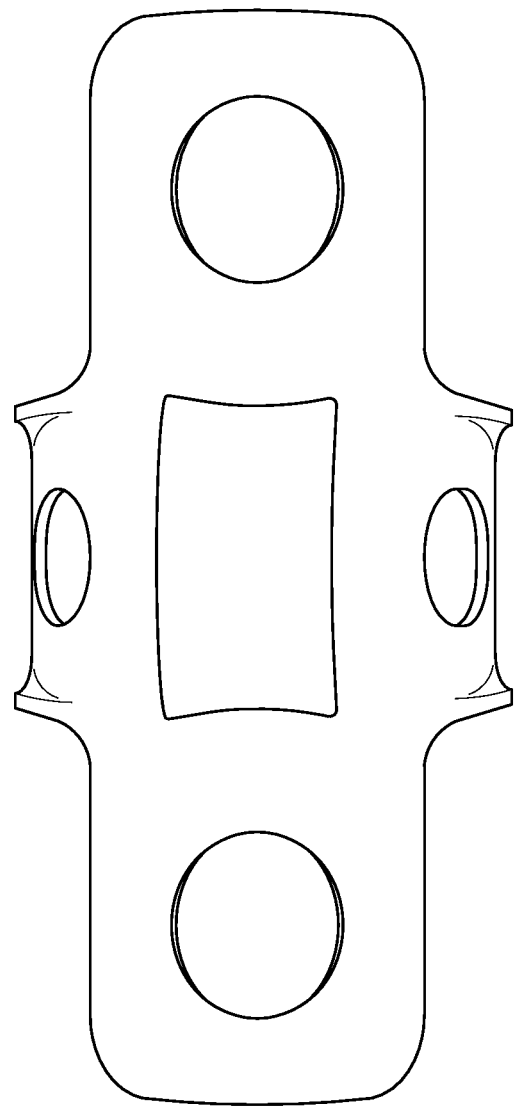
Figure 12C:
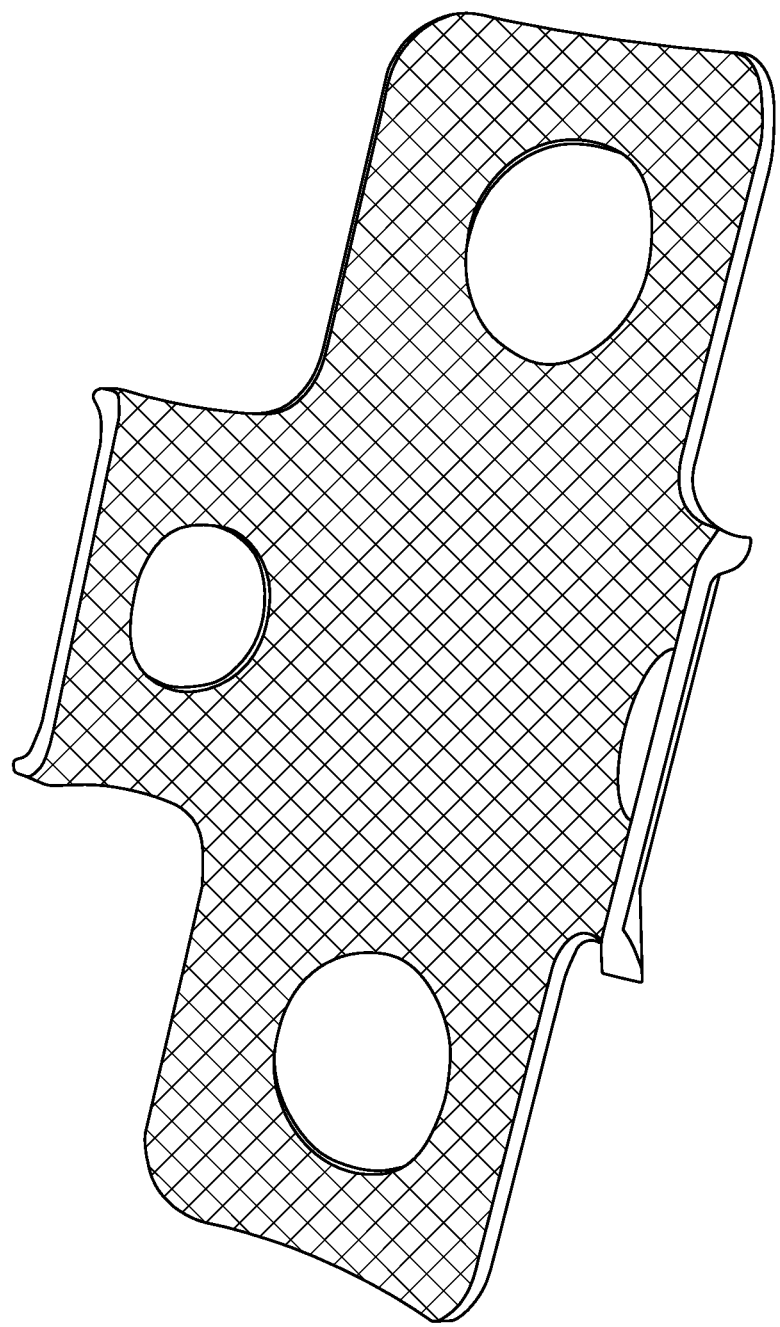
Figure 12D:
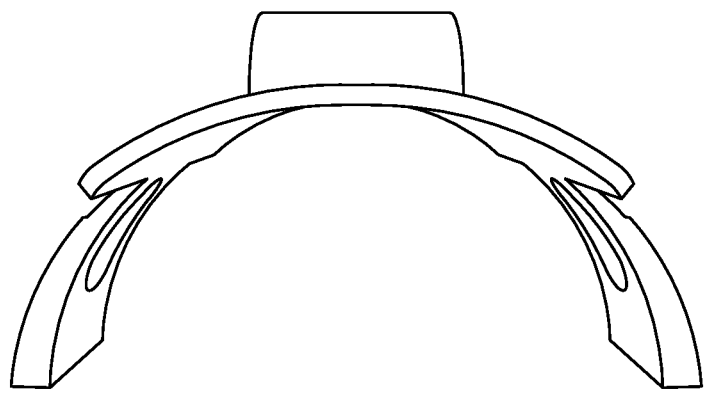
Figure 12E:
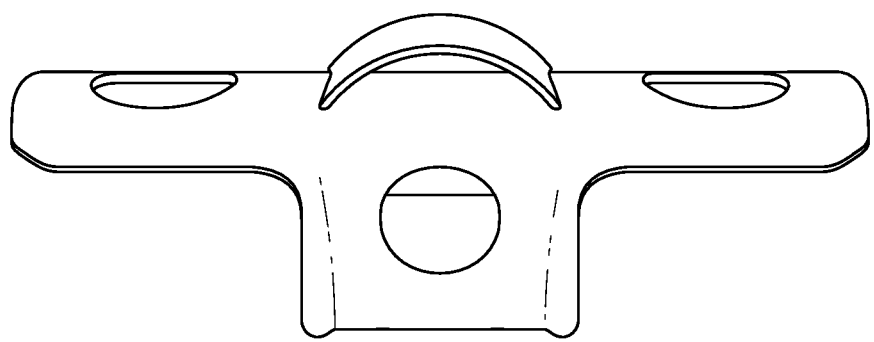

FIGS. 12A-E illustrate another embodiment of a winged looped plate. FIG. 12A shows a side perspective view of a winged looped plate, FIG. 12B shows a top view, FIG. 12C shows a bottom perspective view, FIG. 12D shows an end view, and FIG. 12E shows a side view. As illustrated, the winged looped plate of FIGS. 12A-E is similar to that described above, with some modification. For example, the dorsal loop assumes a more rounded and low-profile shape. The bottom or inner surface (FIG. 12C) has a roughened surface to promote traction against the bone. Raised ridges or flanges are disposed along the buttress wings, configured to maintain the position of the suture over the buttress wings when passed through the transverse opening created by the dorsal loop. In various embodiments, different suture retention mechanisms can be employed, such as flanges, ridges, grooves, or other structures configured to restrain the position of the suture over the buttress wing, for example, to center the suture on the outer surface of the plate body. In the illustrated embodiment (see FIG. 12D) the curvature of the plate body and buttress wings is substantially semi-tubular. In other embodiments, however, the curvature may take other forms. For example, in some embodiments the plate body may be substantially semi-tubular, and the buttress wings may extend at an angle discontinuous from the semi-tubular shape of the plate body. In other embodiments, the plate body may be substantially flat, and the buttress wings may extend therefrom with either flat or curved configurations. The buttress wings can be symmetrical in some embodiments, while in other the two may be asymmetrical. The illustrated embodiment of FIGS. 12A-E includes four holes—two in the plate body and two in the buttress wings. In some embodiments, fewer or more holes may be included. In some embodiments, for example, the winged looped plate may include zero, one, two, three, four, or more holes.

The Method

Disclosed herein are methods for reducing an angular deformity between two bones, by tethering them together using suture tape, a winged looped plate, and tenodesis/interference screws. Specifically, the method may be used for the correction of metatarsus primus adductus, which is the etiology of a bunion deformity.

In some embodiments, the method can be carried out as follows.

1. Locating an unstable bone (1st metatarsal) near a stable bone (2nd metatarsal).
2. Folding one strand of suture tape upon itself to create a double stranded piece, where one end becomes the "looped" end of suture tape, and the other end consists of two free ends of suture tape.
3. Making a small dorsal incision overlying the 2nd metatarsal bone.
4. Passing the double stranded suture tape around the second metatarsal, entering and exiting through the dorsal incision.
5. Passing the free ends of the suture tape through the fixed dorsal loop (eyelet) of the winged looped plate.
6. Sliding the plate down the suture tape, into the dorsal incision and placing it up against the lateral cortex of the 2nd metatarsal.
7. Passing the free ends of the suture tape through the other "looped" end of the suture tape and then pulling on the free ends such that the suture tape becomes tightened in a cow-hitch knot (i.e. luggage tie) fashion around the second metatarsal and winged looped plate.
8. With tension being applied to keep the suture tape snug around the second metatarsal and winged looped plate, the free ends of the suture tape are passed through a soft tissue corridor across the first interspace then through a drill hole in the first metatarsal (from lateral to medial).
9. The wide intermetatarsal angle is reduced to anatomic position manually (or by using a specialized lobster claw bone clamp) while the free ends of the suture are pulled tightly as they exit the hole along the medial cortex of the first metatarsal.
10. A tenodesis screw is inserted into the same drill hole, from medial to lateral, creating interference-type fixation of the suture tape within the metatarsal.
11. With the deformity reduced, the remaining free ends of the same suture tape are passed through a more proximal drill hole within the first metatarsal and passed from medial to lateral.
12. A second tenodesis screw is inserted, from medial to lateral, through the proximal drill hole, securing the second portion of the suture tape to the metatarsal as an adjunctive fixation to the first (distal) drill hole.

The Apparatus:

A winged looped plate may be used in the above described procedure, for protection of the second metatarsal from friction (rope burn) and to distribute the tension forces along a longer area. Pressure is defined as force over area. Increasing the longitudinal area (footprint) of the plate against the metatarsal can distribute and lessen the tension forces applied when the rope is tightened.

In some embodiments, features of the winged loop plate include one or more of the following:

1. A plate body, with two wings extending out in opposite direction from each other, from the center portion of the plate body. Together, the plate body and the extension wings follow the curvature of a long bone such as the second metatarsal.
2. Centered along the outer surface of the plate body, and equally between the wings, is a fixed loop, through which the suture tape or cerclage material is passed as it is tied around the bone and plate together.
3. The fixed loop may act as an eyelet, to keep the suture in place, centered on the plate in both the transverse and longitudinal axes. In some embodiments, the fixed loop can assume as low a profile as possible to avoid excessive protrusion into the second intermetatarsal space and structures therein.
4. The wings of the plate may have ridges or flanges along the longest edges, to keep the suture tape or cerclage material centered on the wing as it ties completely around the bone and plate. These ridges or barriers may also allow the suture tape to be recessed into the width of the wings. Other suture retention mechanisms may be employed, for example a groove disposed within the center of the wings of the plate, configured to receive a suture therein.
5. The winged looped plate may have a roughened undersurface (the surface in direct contact with the bone) (see FIG. 12C). This can provide traction of the plate against the bone and reduce slipping of the plate along the smooth periosteum. The roughened undersurface may be created by plasma-coating, nail file-like roughness, or tack-like micro projections.
6. The plate body and the wings of the plate may have holes for several purposes:
   a. To permit ingrowth/outgrowth of tissue to improve the "anchoring" of the plate against the bone for long term stability of the plate b. To reduce the total plate-to-bone contact surface area, which is important for the protection the vascular supply to the bone and prevent strangulation of the periosteum.

c. One of the holes described may be modified to allow use of a set screw, to secure the plate to one cortex only for the purpose of securing plate position while soft tissue ingrowth occurs.

7. Other proposed uses include Tailors Bunion correction or any other human or veterinary surgical application in which an unstable bone may be anchored to a more stable bone using a variety of cerclage materials.

8. Other embodiments of the plate, including an elongated version with repeating wings and loops may be used for cerclage stabilization of long bone fractures.

FIGS. 13A-13D illustrate another embodiment of a device 400 that may be used for correcting bone deformities, for example, to treat metatarsus primus adductus. FIG. 13A shows an end view of the device 400, FIG. 13B shows a side view, FIG. 13C shows a top perspective view, and FIG. 13D shows a top view. Like the embodiments illustrated in FIGS. 1-5, 9-10, and 12A-12E, this embodiment includes an elongate plate body 402, buttress wings 404, and a transverse opening 410. The transverse opening 410 can also be considered an aperture, eyelet, slot, or the like. The plate body 402 has a first end 422 (which may also be referred to as a proximal end), a second end 424 (which may also be referred to as a distal end), and a longitudinal axis extending between the first end 422 and second end 424. The plate body 402 also has first 426 and second 428 lateral sides that extend between the first 422 and second 424 ends. As illustrated, the lateral sides are straight and extend parallel or substantially parallel with the longitudinal axis, but in other embodiments, the sides may have different shapes such as curved or may be angled relative to each other. In use, an inner surface of the plate body 402 (shown as the lower surface in FIGS. 13A and 13B) engages a bone such as the second metatarsal, for example such that the longitudinal axis is parallel or substantially parallel with the length of the second metatarsal. Although FIGS. 13A and 13B illustrate the inner surface of the plate body 402 as being flat or substantially flat, in other embodiments (such as illustrated in FIG. 12D), the inner surface of the plate may be concave.

A first buttress wing 404 extends away from the first lateral side 426 and the second buttress wing 404 extends from the second lateral side 428. As illustrated in FIG. 13D, when viewed from the top the buttress wings 404 can extend perpendicularly or generally perpendicularly to the longitudinal axis of the plate body 402. The buttress wings 404 can also be centrally located between the first 422 and second 424 ends of the plate body 402, such that the portion of the plate body between the buttress wings and the first end 422 has the same longitudinal length as the portion of the plate body between the buttress wings and the second end 424. In the illustrated embodiment, a longitudinal length of each of the buttress wings 404 is shorter than a longitudinal length of the plate body 402 between the first 422 and second 424 ends.

The buttress wings 404 have inner surfaces that are configured to engage a bone such as the second metatarsal in use and at least partially face each other as shown in FIG. 13A. In one embodiment, the buttress wings 404 are configured to engage opposite sides of the second metatarsal such that the second metatarsal is at least partially surrounded by the elongate plate body 402 and the two buttress wings 404. When the device is viewed from either end or from either side as shown in FIGS. 13A and 13B, the buttress wings extend downwardly from the plate body 402. As the buttress wings 404 extend downwardly away from the plate body 402, the buttress wings preferably spread farther apart from each other, such that lower portions of the buttress wings are farther apart from each other than upper portions of the buttress wings. While FIG. 13A illustrates that the buttress wings may have inner surfaces that are straight or substantially straight, in other embodiments, such as shown in FIG. 12D, the inner surfaces may be concave. In one embodiment, when both the inner surface of the plate body 402 and the inner surfaces of the buttress wings 404 are concave, the inner surface of the plate body may have the same or a larger radius of curvature than the inner surfaces of the buttress wings.

As with previous embodiments, one or more transverse openings may be located between the first end second ends of the plate body. As illustrated in FIGS. 13A-13D, a transverse opening 410 may be located between the first 422 and second 424 ends of the plate body 402 that extends perpendicularly or substantially perpendicularly to the longitudinal axis. As shown, the transverse opening 410 can be centrally located between the first 422 and second 424 ends of the plate body 402. The transverse opening 410 is aligned with the buttress wings 404. In use, when the device 400 is placed against the second metatarsal and cerclage material is passed through the transverse opening 410 to fix the cerclage material to the patient's first metatarsal, the cerclage material extends over the buttress wings 404. The buttress wings 404 advantageously maintain a separation of the cerclage material from the bone and therefore protect the bone from the cerclage material.

The buttress wings 404 can include raised ridges or flanges 430 extending parallel to the transverse opening along the outer edges of the buttress wings 404. The raised ridges or flanges 430 are configured to maintain the position of the cerclage material over the buttress wings 404 when passed through the transverse opening 410. In various embodiments, different cerclage retention mechanisms can be employed, such as flanges, ridges, grooves, or other structures configured to restrain the position of the cerclage material over the buttress wings 404. For example, in other embodiments, a center portion of the buttress wings 404 can be recessed from the outer edges to form a channel or groove for the cerclage material.

In some embodiments, the device does not include a transverse opening, and the ridges or flanges 430 or other retention mechanism extend across the plate body 402 as well. In other words, the ridges, flanges, groove, or other structure can extend continuously across the buttress wings 404 and plate body 402 to form a channel, tunnel, or the like for positioning the cerclage material and keeping the cerclage material extending across the wings 404. For example, ridges, flanges or a groove may extend along a center portion of the plate body transverse to the longitudinal axis, either with or without ridges, flanges or a groove also extending along the wings.

In some embodiments, the transverse opening 410 is at least partially defined by a dorsal loop 406. In one embodiment, as best illustrated in FIG. 13B, the dorsal loop 406 comprises an upper wall that is positioned above the outer or upper surface of the plate body and side walls connecting the upper wall to the plate body, so that the transverse opening 410 is formed below the upper wall and between the side walls. The dorsal loop 406 can be fixed and immobile relative to the plate body 402. In the illustrated embodiment, the plate body 402, buttress wings 404, and dorsal loop 406, or at least the inner surfaces thereof, are substantially flat or straight. In other embodiments, any or all of the plate body 402, buttress wings 404, and dorsal loop 406 can have curved, tubular, semi-tubular, or other configurations. In the illustrated embodiment, the dorsal loop 406 is completely enclosed when viewed from the side. In some alternative embodiments, the dorsal loop 406 can be partially open or only partially enclosed when viewed from the side. In some such embodiments, the cerclage material can be inserted downward into the dorsal loop 406 through the partial opening rather than being threaded through from the side.

In some embodiments, the plate body 402, buttress wings 404, and dorsal loop 406 are integrally formed from a single piece of material, such as metal. In some such embodiments, the device 400 is manufactured by stamping. In other embodiments, the device 400 can be manufactured by 3-D printing and can be made of a plastic material such as PEEK. In other embodiments, the plate body and the buttress wings may be integrally formed from a single piece of material, and a dorsal loop may be attached to an outer or upper surface of the plate body.

In some embodiments, particularly for use with the second metatarsal, the plate body 402 has a longitudinal length of about 19 mm to about 25 mm, for example, about 22 mm. The plate body 402 can have a width of about 5 mm to about 8 mm. The device 400 including the plate body 402 and buttress wings 404 can span a width of about 13 mm to about 15 mm (for example, as measured by the span between the lower ends of the buttress wings). The buttress wings 404 can have a width (or a longitudinal length, in a direction parallel to the longitudinal axis of the plate body 402) of about 5 mm to about 11 mm, for example, about 8 mm.

Like the embodiments illustrated in previous Figures, the device 400 can include holes 408 in the plate body 402 and/or buttress wings 404. Such holes may be used for ingrowth of tissue, or may simply be used to reduce the weight of the device. As shown, the plate body 402 can also include an opening 412 through the portion of the plate body 402 between the buttress wings 404. In some embodiments, the opening 412 can be sized to allow a buffer or similar tool to reach the inner surface of the dorsal loop 406 to make the inner surface smooth. A smooth inner surface can advantageously help reduce friction, damage, or wear on the cerclage material passed through the dorsal loop 406. Although in the illustrated embodiment a width of the opening 412 is about the same as a width of the plate body 402, in other embodiments, the openings 412 can be narrower or have a smaller width. In other embodiments the plate body 402 and/or buttress wings 404 do not include any holes 408 and/or the opening 412.

Figure 14:
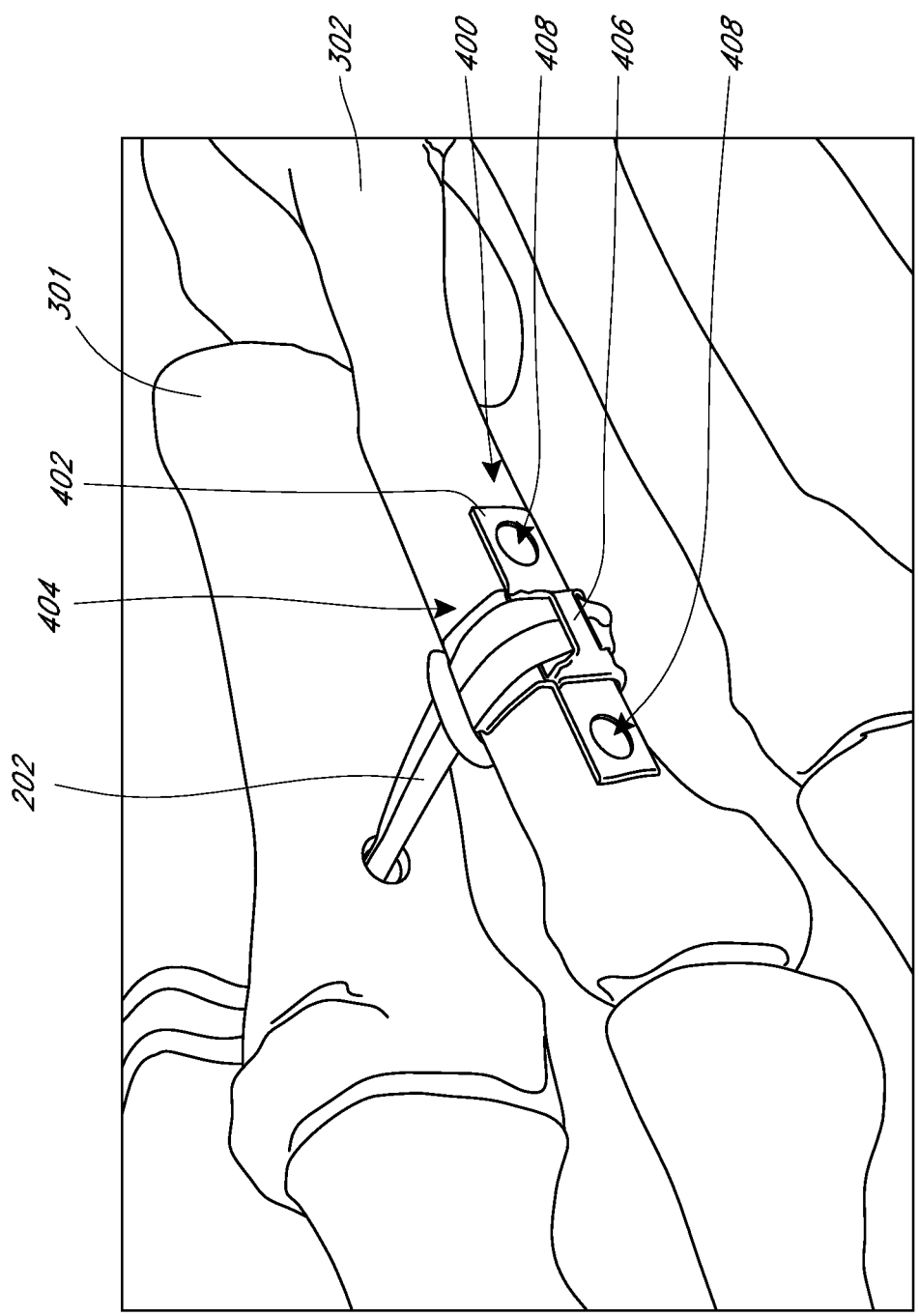
FIG. 14 shows an example embodiment of a method of using the device of FIGS. 13A-13D.

FIG. 14 partially illustrates an example embodiment of a method of using the device 400 of FIGS. 13A-13D to correct the angular bone deformity, such as metatarsus primus adductus. As described with respect to previous embodiments, the device 400 is placed with the inner surface against the stable bone 302 (such as the second metatarsal) and with the plate body 402 and transverse opening 410 positioned on a lateral side of the stable bone 302. The cerclage material 202 is passed through the transverse opening 410 of the device 400 on the stable bone 302 and tied around the stable bone 302 and device 400 using a cerclage technique. The device 400 can therefore be fixed to the second metatarsal without drilling a hole in the second metatarsal. The free ends of the cerclage material 202 are passed through the hole in the unstable bone 301 and tension is applied to the cerclage material 202 to reduce the angular bone deformity. In some embodiments, the device 400 can be provided in a kit with, for example, cerclage material, one or more screws configured to fix the cerclage material to the unstable bone or first metatarsal, and/or a suture passing instrument.

Figure 15A:
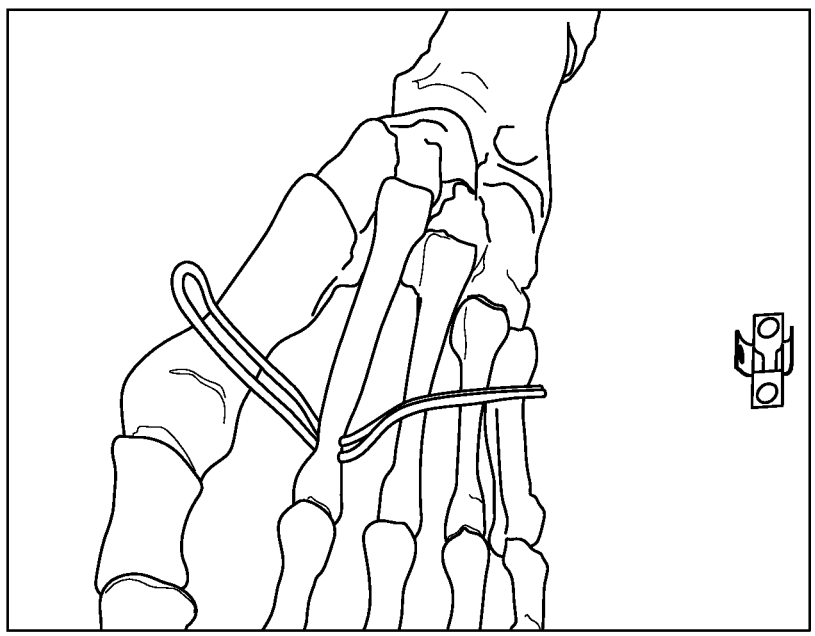
FIGS. 15A-15P illustrate steps of a method utilizing a bone plate having buttress wings for correction of inter-metatarsal angle deformity.
Figure 15B:
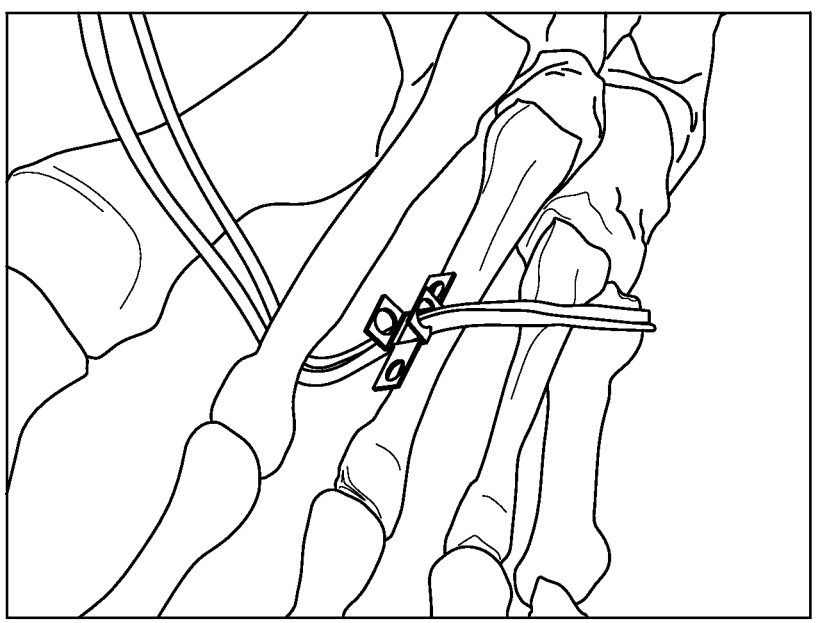
Figure 15C:
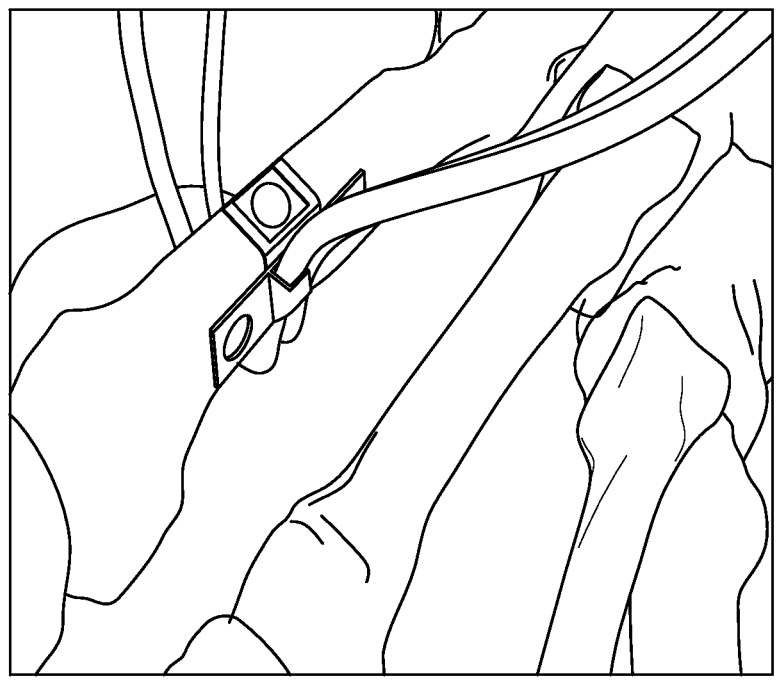
Figure 15D:
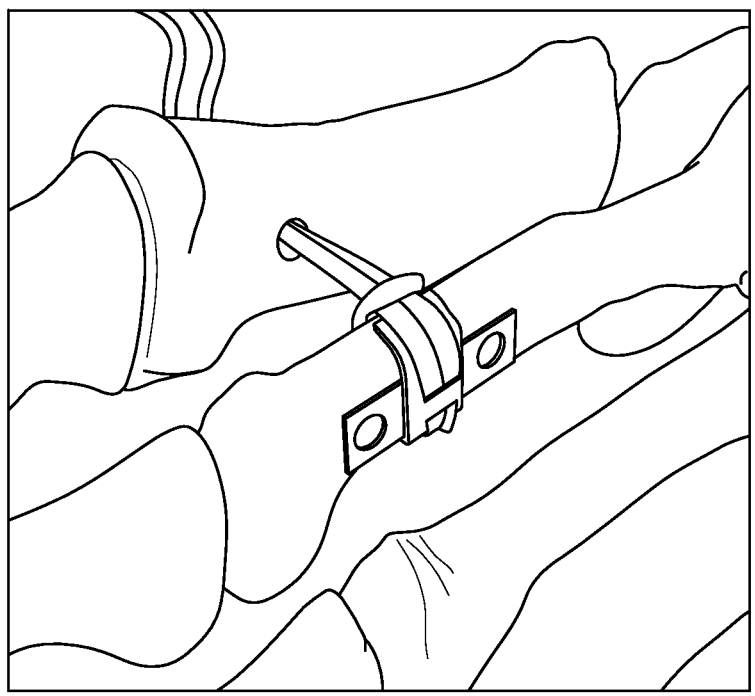
Figure 15E:
Figure 15F:
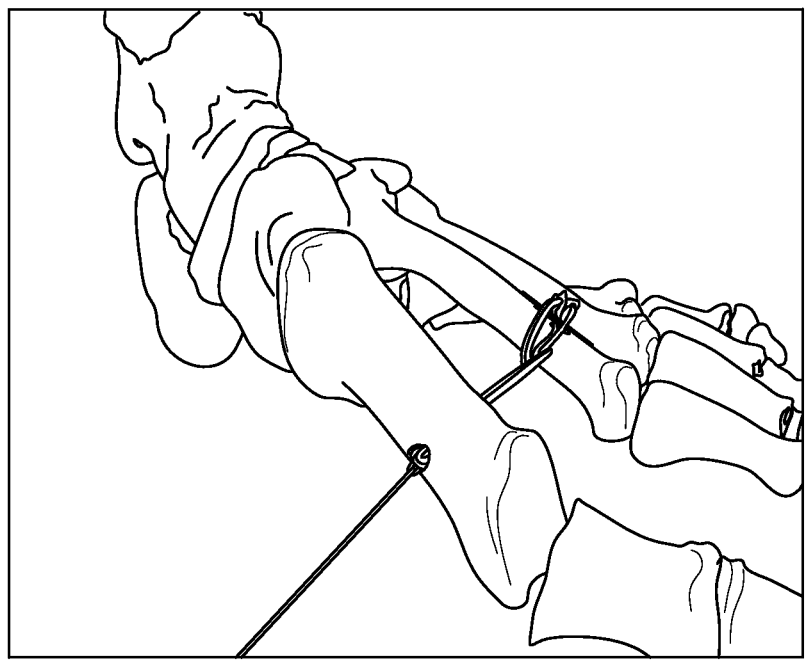
Figure 15G:
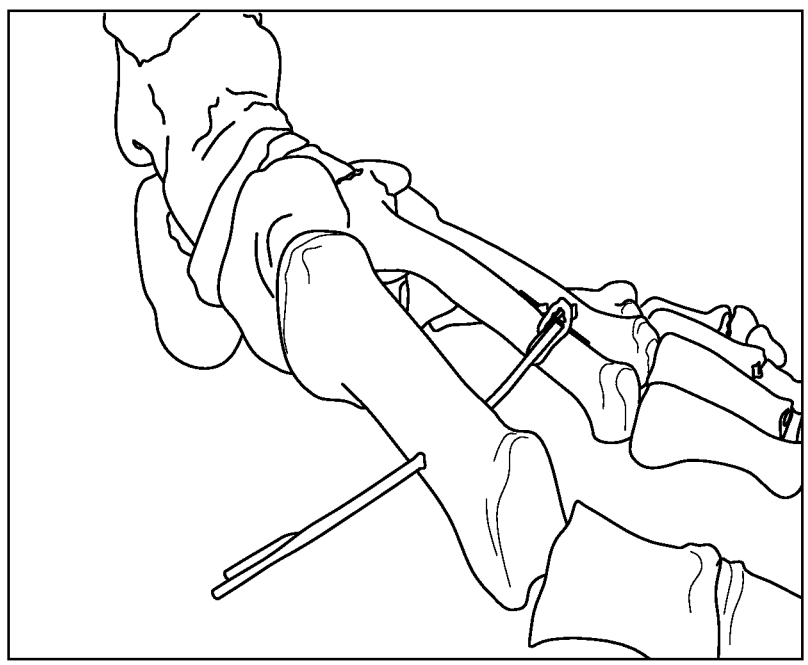
Figure 15H:
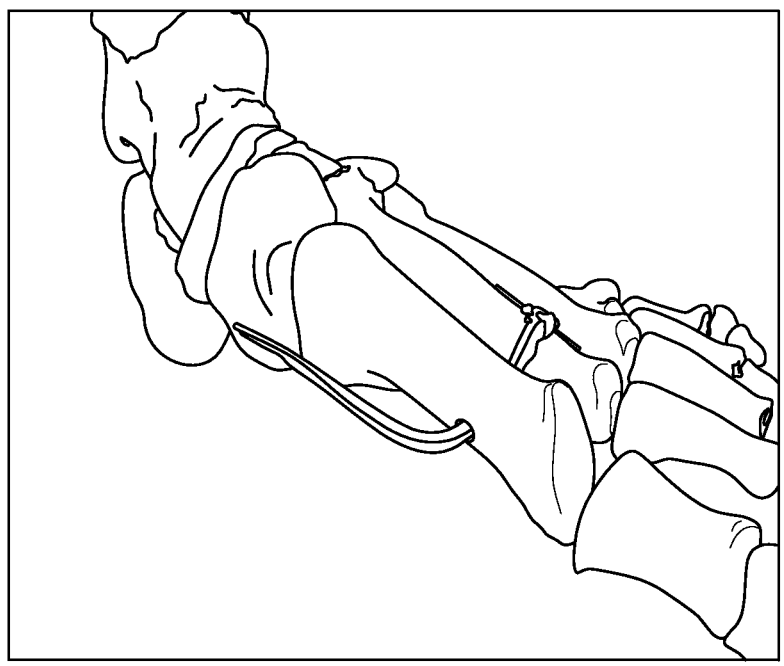
Figure 15I:
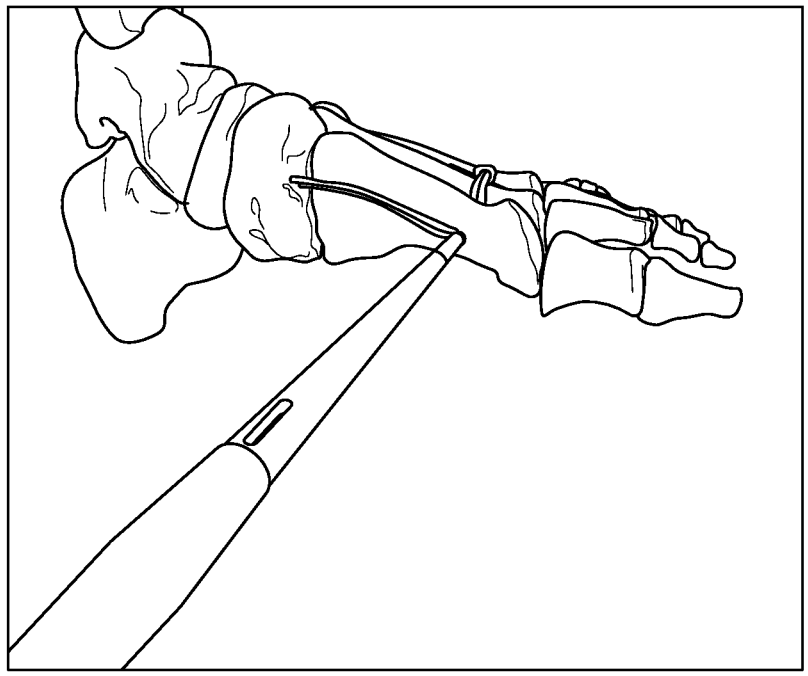
Figure 15J:
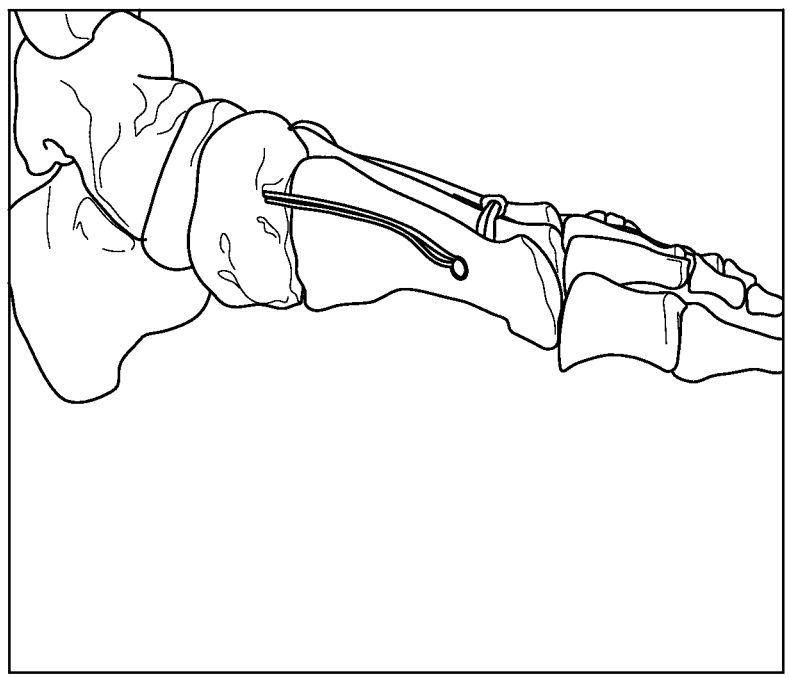
Figure 15K:
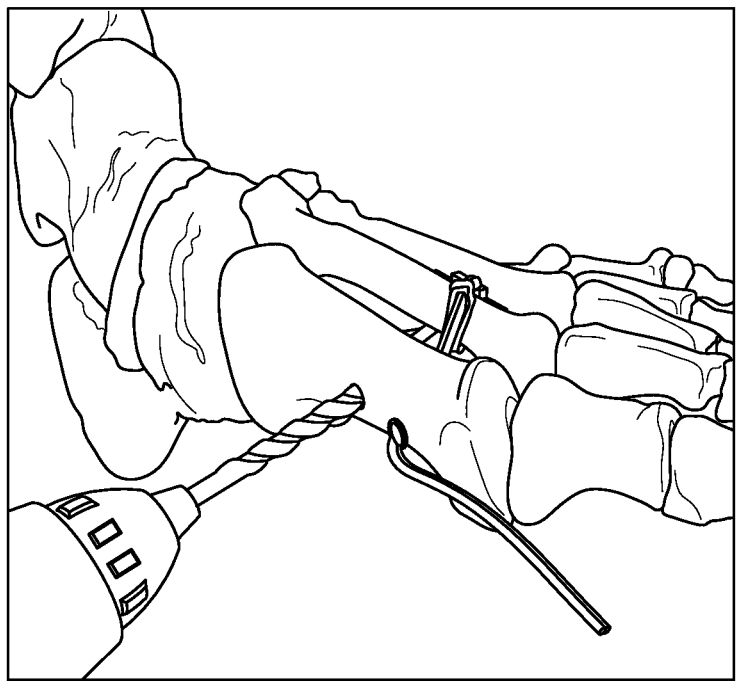
Figure 15L:
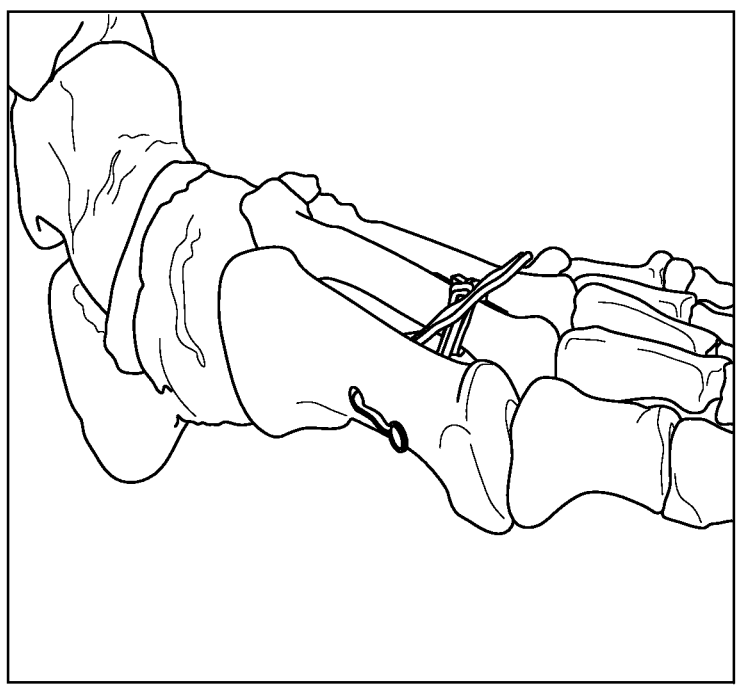
Figure 15M:
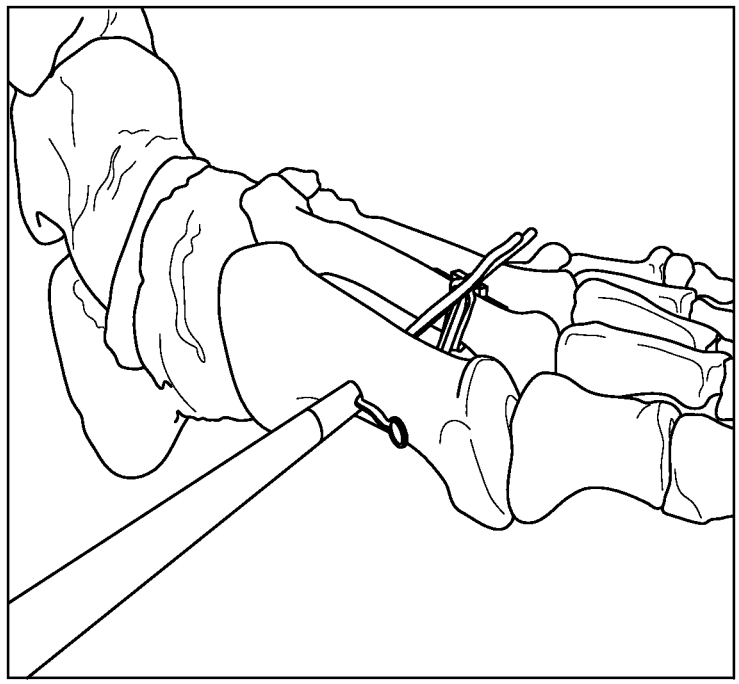
Figure 15N:
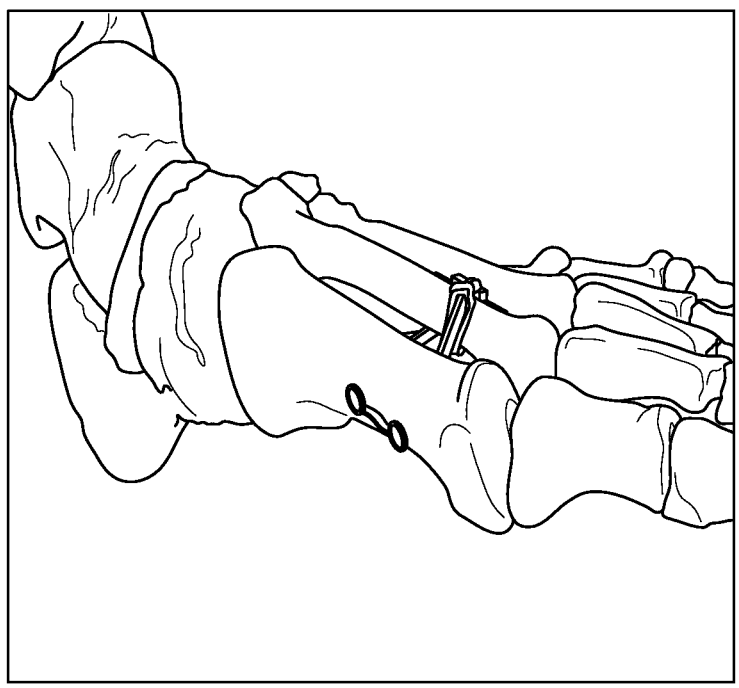
Figure 15O:
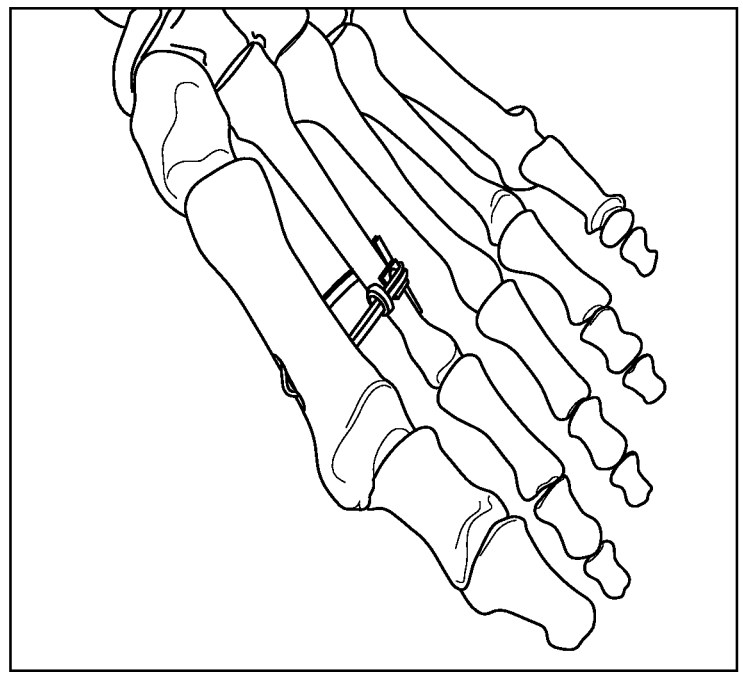
Figure 15P:
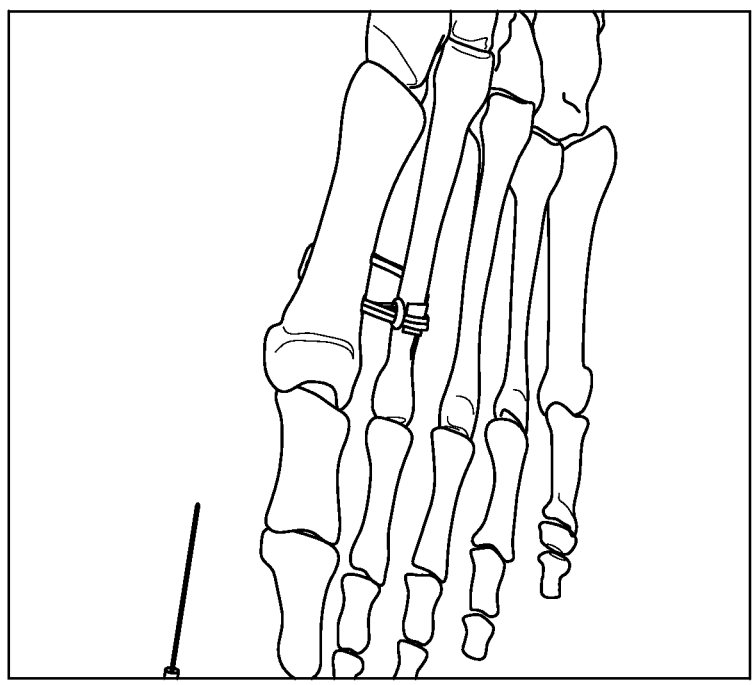

FIGS. 15A-15P illustrate the steps of one embodiment of a method for correction of inter-metatarsal angle deformity. In this illustrated embodiment, cerclage material such as suture tape is utilized with a winged looped plate on the second (stable) metatarsal, and a knotless anchor fixates (couples) the cerclage material to the first (unstable) metatarsal. In FIG. 15A, cerclage material is passed around the second metatarsal. In FIG. 15B, the cerclage material is threaded through the dorsal loop of a winged looped plate as described previously herein. The plate is placed against the second metatarsal bone, with the long axis of the plate aligned with the long axis of bone. The buttress wings extend outward, aligned with dorsal loop, around dorsal and plantar cortices of the second metatarsal. The dorsal loop defines a channel transverse to the longitudinal axis, through which the cerclage material is passed.

As shown in FIG. 15C, cerclage material is tied around both the second metatarsal bone and the winged looped plate. Wings follow the circumferential path of the cerclage material. As shown in FIG. 15D, cerclage material extends over the buttress wings. Wings are situated between cerclage material and bone, reducing total contact area between the cerclage material and bone. This provides a buttress effect.

As shown in FIG. 15E, a hole is drilled through the first metatarsal bone. As shown in FIG. 15F, the free ends of cerclage material are pulled through the drill hole from a lateral to medial direction. As shown in FIGS. 15G-15H, the cerclage material is tensioned and the angular deformity is reduced between the first and second metatarsal bones.

Next, the cerclage material is secured to the first metatarsal bone. As shown in FIG. 15I, this may comprise inserting an interference screw into the drill hole in first metatarsal, with tensioned cerclage material inside the hole. Then, as shown in FIG. 15J, interference screw fixation using an interference screw inserted into the hole provides knotless, button-less coupling of cerclage material to the first metatarsal.

In some embodiments, double fixation of the cerclage material in the first metatarsal bone may be utilized. As shown in FIG. 15K, a second drill hole may be made in the first metatarsal bone. As shown in FIG. 15L, cerclage material may be passed through the second hole from a medial to lateral direction. A second interference screw may be inserted into the second hole, as shown in FIGS. 15M and 15N. Double screw fixation of cerclage material into the first metatarsal provides knotless and buttonless fixation.

Figure 16A:
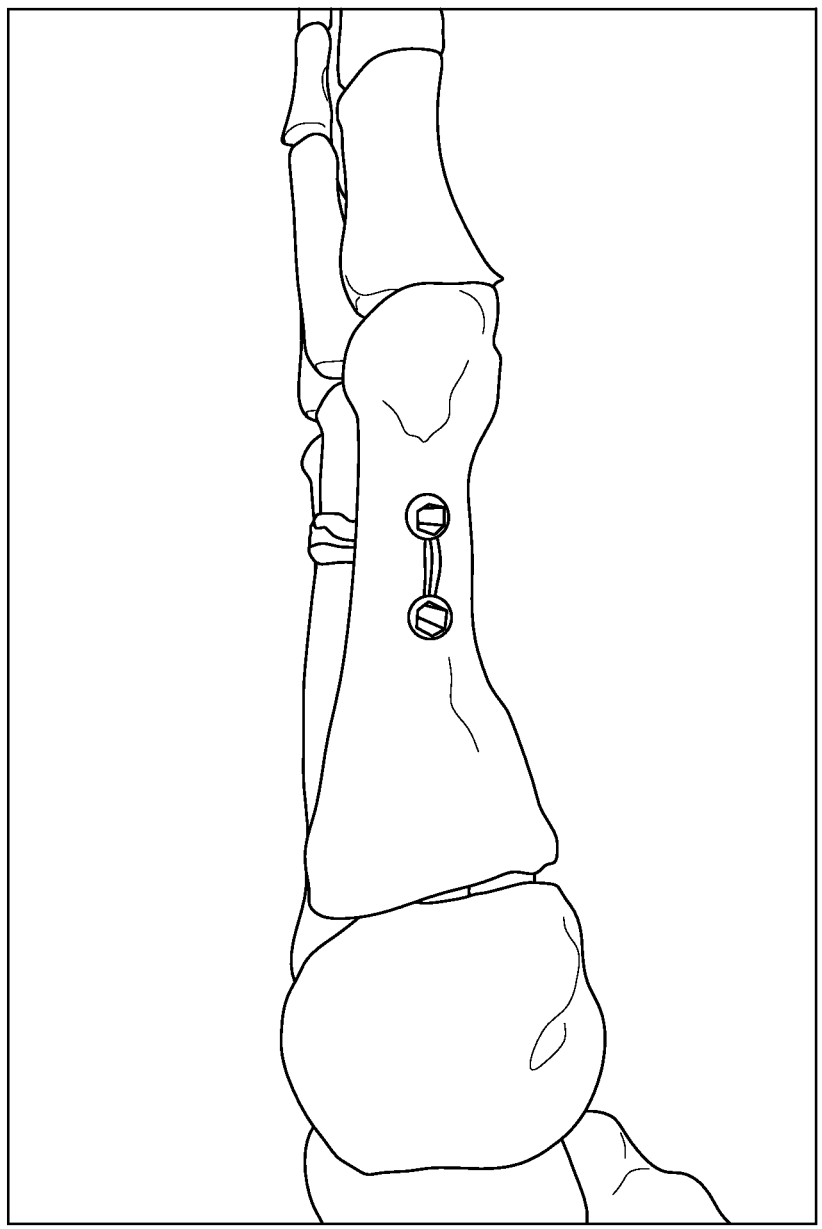
FIG. 16A shows a side view of the first metatarsal after being treated utilizing the method of FIGS. 15A-15P.
Figure 16B:
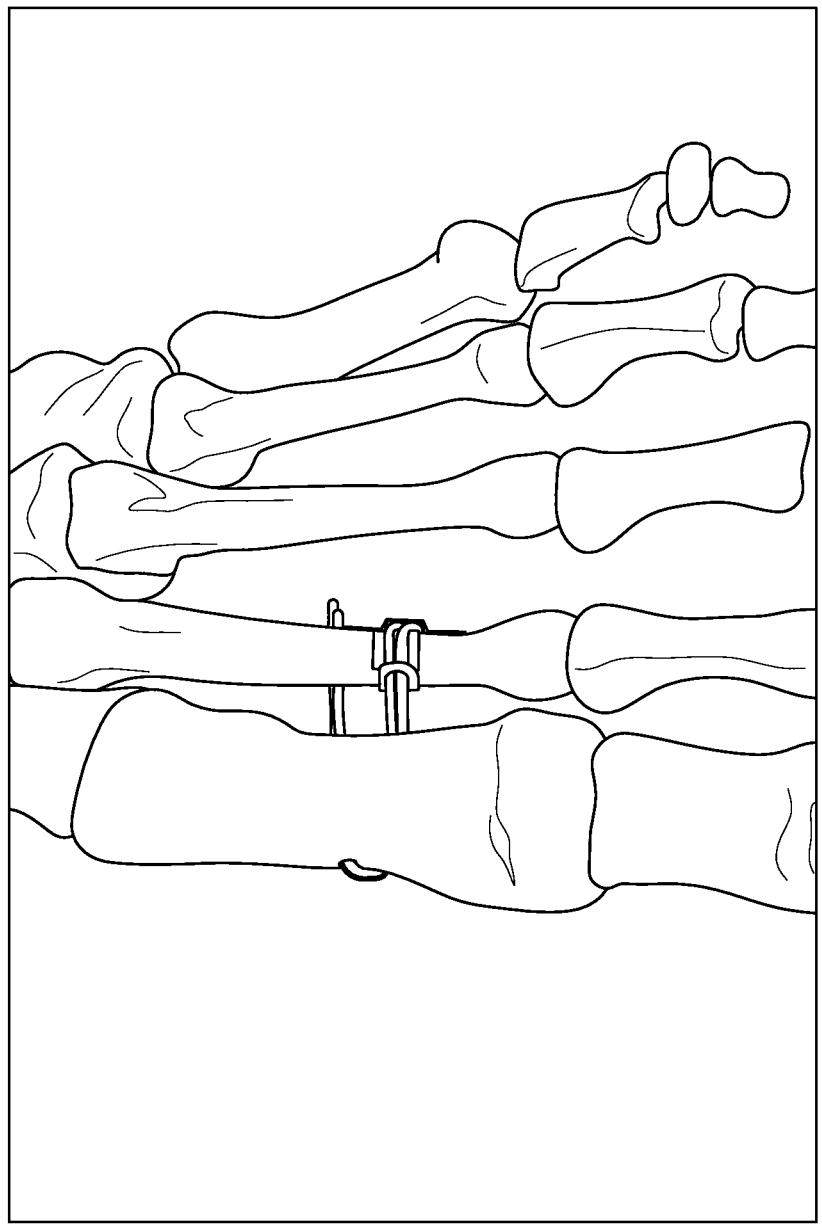
FIG. 16B shows a top view of the foot after being treated utilizing the method of FIGS. 15A-15P.
Figure 16C:
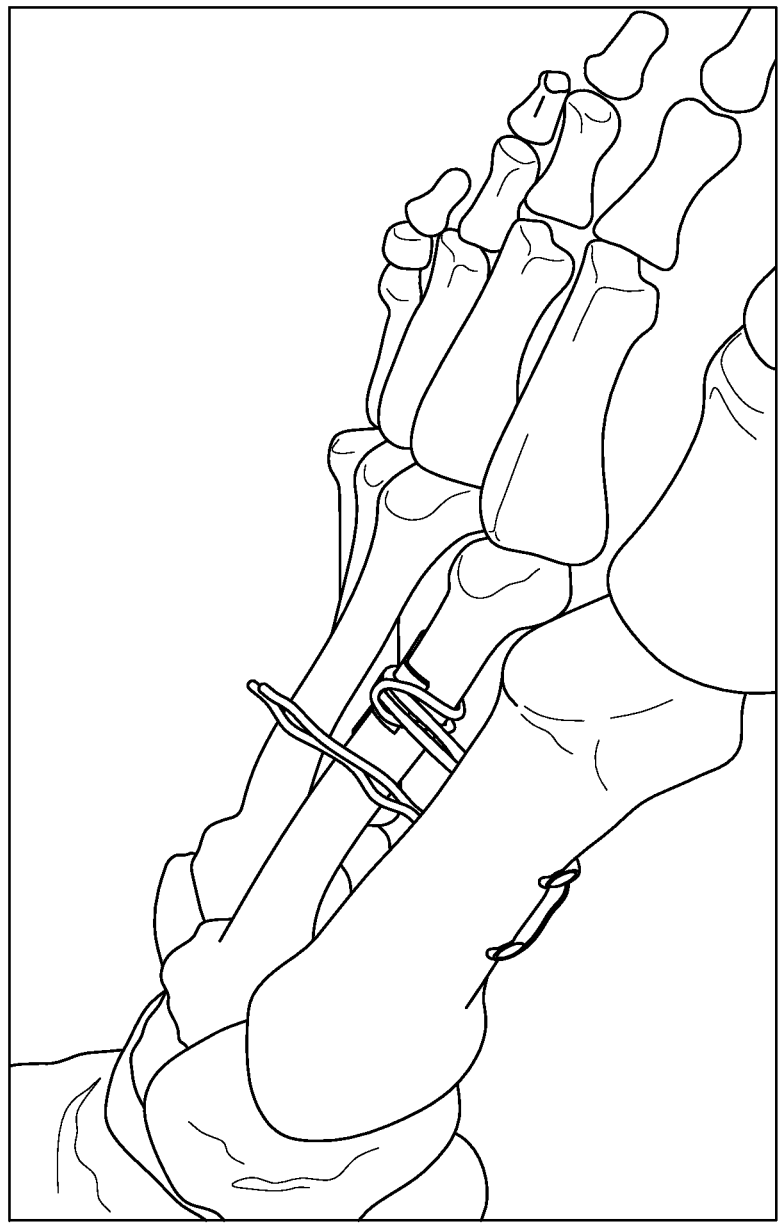
FIG. 16C shows an oblique view of the foot after being treated utilizing the method of FIGS. 15A-15P.

FIGS. 15O and 15P illustrate the foot after the procedure has been completed. The plate body distributes tension forces of cerclage material over the lateral cortex. The buttress wings protect the second metatarsal bone from friction of the cerclage material on the dorsal and plantar cortices. FIGS. 16A-16C illustrate further views of the plate body, cerclage material and interference screws after the procedure has been completed.

All features disclosed in this specification, including any accompanying claim, abstract, and drawings, may be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means for" performing a specified function, or "step for" performing a specific function, is not to be interpreted as a "means" or "step" clause as specified in 35 U.S.C. §112, paragraph 6. In particular, the use of "step of" in the claims herein is not intended to invoke the provisions of 35 U.S.C. §112, paragraph 6.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Although preferred embodiments of the present invention have been shown and described, various modifications and substitutions may be made thereto without departing from the spirit and scope of the invention. Accordingly, it is to be understood that the present invention has been described by way of illustration and not limitation.

What is claimed is:

1. A device for treating an angular bone deformity, comprising:
   an elongate plate body configured to extend along a length of a patient's stable metatarsal, the elongate plate body comprising an inner surface configured to engage the stable metatarsal and an outer surface, wherein the elongate plate body comprises a first end and a second end and a longitudinal axis extending between the first end and the second end, wherein the longitudinal axis is configured to be parallel or substantially parallel with the length of the stable metatarsal;
   two buttress wings extending from opposite sides of the plate body, each of the buttress wings comprising an inner surface configured to engage the stable metatarsal and an outer surface, wherein the inner surfaces of the buttress wings at least partially face each other so that when the plate body and the buttress wings are placed against the stable metatarsal, the stable metatarsal is at least partially surrounded by the elongate plate body and the two buttress wings; and
   a transverse opening located between the first and second ends of the plate body, wherein the transverse opening extends perpendicular to the longitudinal axis and is aligned with the two buttress wings such that when the plate body and the two buttress wings are placed against the stable metatarsal and cerclage material passes through the transverse opening and is tied around the stable metatarsal, and is then secured to the patient's unstable metatarsal, the cerclage material extends over the two buttress wings;
   wherein raised ridges or flanges are disposed along the buttress wings, and a groove is disposed within a center of the wings, such that a thickness of outer edges of the buttress wings measured between the outer surface and the inner surface is greater than a thickness of portions of the buttress wings in the center of the wings, the raised ridges or the flanges or the groove being configured to maintain the position of the cerclage material centered over the wings after the cerclage material passes through the transverse opening.

2. The device of claim 1, wherein the plate body and the two buttress wings have inner surfaces that are flat.

3. The device of claim 1, wherein the plate body and the two buttress wings have inner surfaces that are concave and outer surfaces that are convex.

4. The device of claim 1, further comprising one or more holes in the plate body or the two buttress wings.

5. The device of claim 1, wherein the transverse opening is centrally located between the first end and the second end of the plate body.

6. The device of claim 1, wherein the transverse opening is defined at least in part by a dorsal loop provided on or above the outer surface of the plate body.

7. The device of claim 6, wherein the dorsal loop comprises a curved wall extending above the outer surface of the plate body.

8. The device of claim 6, wherein the dorsal loop comprises a flat wall extending above the outer surface of the plate body.

9. The device of claim 6, wherein the plate body comprises a hole between the first end and the second end beneath the dorsal loop.

10. The device of claim 6, wherein the dorsal loop is fixed and immobile relative to the plate body.

11. The device of claim 6, wherein the plate body, the two buttress wings and the dorsal loop are integrally formed from a single piece of material.

12. The device of claim 1, wherein the two buttress wings are symmetrically positioned about the longitudinal axis.

13. The device of claim 1, wherein the two buttress wings are centrally located between the first and second ends of the plate body.

14. The device of claim 1, wherein a longitudinal length of each of the buttress wings is shorter than a longitudinal length of the plate body between the first end and the second end.

15. The device of claim 1, comprising multiple pairs of buttress wings longitudinally spaced along the length of the plate body.

16. The device of claim 1, wherein the buttress wings are configured to prevent cerclage material from directly contacting the stable metatarsal when cerclage material extends through the transverse opening to fix the free ends of the cerclage material to the patient's unstable metatarsal.

17. The device of claim 1, wherein each of the buttress wings extends outwardly away from the longitudinal axis.

18. The device of claim 1, wherein each of the buttress wings extends in a direction perpendicular or generally perpendicular to the longitudinal axis.

19. The device of claim 1, wherein the plate body comprises first and second lateral sides extending parallel or substantially parallel with the longitudinal axis, wherein a first of the two buttress wings extends away from the first lateral side and a second of the two buttress wings extends away from the second lateral side.

20. The device of claim 1, wherein the two buttress wings are configured to engage opposite sides of the stable metatarsal.

21. The device of claim 1, wherein the plate body is configured to engage a lateral side of the stable metatarsal and be fixed relative thereto without drilling a hole in the stable metatarsal.

22. The device of claim 1, wherein the plate body and the two buttress wings are configured to at least partially surround the second metatarsal.

23. A system for treating an angular bone deformity, comprising the device of claim 1, and further comprising cerclage material configured to extend through the transverse opening and configured to fix the stable metatarsal relative to the unstable metatarsal.

24. The system of claim 23, further comprising one or more screws configured to fix the cerclage material to the unstable metatarsal.

25. The system of claim 23, further comprising a suture passing instrument.

* * * * *